United States Patent
Alizad et al.

(10) Patent No.: US 12,207,973 B2
(45) Date of Patent: Jan. 28, 2025

(54) SYSTEMS AND METHODS FOR MICROVESSEL ULTRASOUND IMAGING

(71) Applicant: Mayo Foundation for Medical Education and Research, Rochester, MN (US)

(72) Inventors: Azra Alizad, Rochester, MN (US); Mostafa Fatemi, Rochester, MN (US); Rohit Nayak, Rochester, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 635 days.

(21) Appl. No.: 17/422,384

(22) PCT Filed: Jan. 13, 2020

(86) PCT No.: PCT/US2020/013333
§ 371 (c)(1),
(2) Date: Jul. 12, 2021

(87) PCT Pub. No.: WO2020/146880
PCT Pub. Date: Jul. 16, 2020

(65) Prior Publication Data
US 2022/0087651 A1 Mar. 24, 2022

Related U.S. Application Data

(60) Provisional application No. 62/791,511, filed on Jan. 11, 2019, provisional application No. 62/846,983, (Continued)

(51) Int. Cl.
*G06T 11/00* (2006.01)
*A61B 8/08* (2006.01)
(Continued)

(52) U.S. Cl.
CPC ......... *A61B 8/5207* (2013.01); *A61B 8/0891* (2013.01); *A61B 8/5223* (2013.01);
(Continued)

(58) Field of Classification Search
CPC ................. G06T 7/0012; G06T 11/003; G06T 2207/30004
See application file for complete search history.

(56) References Cited

U.S. PATENT DOCUMENTS 7,978,932 B2 * 7/2011 Vercauteren .......... G06T 3/4038
382/284
2009/0187106 A1 * 7/2009 Lee ..................... G01S 15/8963
600/458
(Continued)

FOREIGN PATENT DOCUMENTS

WO 2018213839 A2 11/2018
WO 20180222724 A1 12/2018

OTHER PUBLICATIONS

Adabi, S., et al., "Non-Local Based Denoising Framework for In Vivo Contrast-Free Ultrasound Microvessel Imaging" Sensors (2019) 19 245.
(Continued)

*Primary Examiner* — Kevin Ky
(74) *Attorney, Agent, or Firm* — Quarles & Brady LLP

(57) ABSTRACT

Described here are systems and methods for generating microvessel images from image data acquired with an ultrasound system while analyzing the image data in real-time, or retrospectively, to generate a performance descriptor that can be used to assess data quality and/or motion correction quality; to adaptively suppress noise in the data; or both.

30 Claims, 16 Drawing Sheets

Related U.S. Application Data filed on May 13, 2019, provisional application No. 62/936,852, filed on Nov. 18, 2019.

(51) Int. Cl.
  *G06T 7/00* (2017.01)
  *A61B 8/06* (2006.01)

(52) U.S. Cl.
  CPC .......... *G06T 7/0012* (2013.01); *G06T 11/003* (2013.01); *A61B 8/06* (2013.01); *G06T 2207/30004* (2013.01)

(56) References Cited

U.S. PATENT DOCUMENTS

| | | | |
|---|---|---|---|
| 2009/0270738 A1* | 10/2009 | Izatt | A61B 5/0261 600/476 |
| 2013/0090557 A1* | 4/2013 | Takagi | A61B 8/14 600/431 |
| 2015/0208915 A1* | 7/2015 | Schallek | A61B 3/1241 351/246 |
| 2016/0253820 A1* | 9/2016 | Jeanne | G06T 7/0012 382/107 |
| 2018/0220997 A1* | 8/2018 | Song | G16H 50/30 |
| 2020/0163612 A1* | 5/2020 | Ntziachristos | A61B 5/7207 |
| 2020/0178939 A1* | 6/2020 | Song | A61B 8/5223 |
| 2020/0187910 A1* | 6/2020 | Pinton | A61B 8/085 |
| 2020/0375571 A1* | 12/2020 | Lorraine | A61B 8/4254 |

OTHER PUBLICATIONS

Baranger, J., et al., "Adaptive spatiotemporal SVD clutter filtering for Ultrafast Doppler Imaging using similarity of spatial singular vectors," IEEE Transactions on Medical Imaging (2018) 37(7), 1574-1586.

Bayat, M., et al., "Background Removal and Vessel Filtering of Non-Contrast Ultrasound Images of Microvasculature" IEEE Transactions on Biomedical Engineering (2019) 66 pp. 831-842.

Hansen, HH, et al., "Validation of non-invasive in vivo compound ultrasound strain imaging using histologic plaque vulnerability features" Stroke (2016) 47 pp. 2770-2775.

Harput, S., et al., "Two stage sub-wavelength motion correction in human microvasculature for CELIS imaging" Proc. IEEE Int. Ultrason. Symp. (IUS), (2017) pp. 1-4.

Harput, S., et al., "Two-Stage Motion Correction for Super-Resolution Ultrasound Imaging in Human Lower Limb." IEEE transactions on ultrasonics, ferroelectrics, and frequency control (2018) 65(5), pp. 803-814.

Hingot V., et al., "Subwavelength motion-correction for ultrafast ultrasound localization microscopy." Ultrasonics (2017) 77 pp. 17-21.

Kim, M., et al., "Expanding Acquisition and Clutter Filter Dimensions for Improved Perfusion Sensitivity" IEEE transactions on ultrasonics, ferroelectrics, and frequency control (2017) 64, pp. 1429-1438.

Kim, M., et al., "Multidimensional Clutter Filter Optimization for Ultrasonic Perfusion Imaging" IEEE transactions on ultrasonics, ferroelectrics, and frequency control (2018) 65 pp. 2020-2029.

Larrson, M., et al., "Ultrasound speckle tracking for radial, longitudinal and circumferential strain estimation of the carotid artery-an in vitro validation via sonomicrometry using clinical and high-frequency ultrasound." Ultrasonics (2015) 56:399-408.

International Search Report and Written Opinion issued for PCT/US2020/013333 dated Jun. 23, 2020.

International Preliminary Report on Patentability issued for PCT/US2020/013333 dated Jun. 16, 2021.

Ment, L.R., et al., "Germinal matrix microvascular maturation correlates inversely with the risk period for neonatal intraventricular hemorrhage," Developmental brain research (1995) 84(1), 142-149.

Nayak, R. et al., "Non-Contrast Agent Based Small Vessel Imaging of Human Thyroid Using Motion Corrected Power Doppler Imaging." Scientific Reports (2018) 8(1) p. 15318.

Nayak, R., et al., "Non-invasive Small Vessel Imaging of Human Thyroid Using Motion-Corrected Spatiotemporal Clutter Filtering" Ultrasound in medicine & biology (2019) 45, pp. 1010-1018.

Song, P., et al., "Noise Equalization for Ultrafast Plane Wave Microvessel Imaging." IEEE transactions on ultrasonics, ferroelectrics, and frequency control (2017) 64(11), pp. 1776-1781.

Song, P., et al., "Ultrasound small vessel imaging with block-wise adaptive local clutter filtering." IEEE transactions on medical imaging (2017) 36:251-262.

Tierney, J., et al., "Adaptive clutter demodulation for non-contrast ultrasound perfusion imaging." IEEE transactions on medical imaging (2017) 36:1979-1991.

Vohr, B., et al., "Intraventricular hemorrhage in the preterm infant," Early human development (1996) 44(1), 1-16.

Yu, A., et al., "Eigen-based clutter filter design for ultrasound color flow imaging: a review." IEEE transactions on ultrasonics, ferroelectrics, and frequency control (2010) 57, pp. 1096-1111.

European Patent Office, Extended Search Report, Application No. 23209066.2, Feb. 12, 2024, 7 pages.

\* cited by examiner

SYSTEMS AND METHODS FOR MICROVESSEL ULTRASOUND IMAGING

CROSS-REFERENCE TO RELATED APPLICATIONS

This application is a 371 U.S. National Phase application of PCT/US2020/013333, filed Jan. 13, 2020, which claims the benefit of U.S. Provisional Patent Application Ser. No. 62/791,511, filed on Jan. 11, 2019, and entitled "SYSTEMS AND METHODS FOR GENERATING PERFORMANCE DESCRIPTORS FOR MICROVESSEL ULTRASOUND IMAGING," of U.S. Provisional Patent Application Ser. No. 62/846,983, filed on May 13, 2019, and entitled "SYSTEMS AND METHODS FOR GENERATING PERFORMANCE DESCRIPTORS FOR MICROVESSEL ULTRASOUND IMAGING," and of U.S. Provisional Patent Application Ser. No. 62/936,852, filed on Nov. 18, 2019, and entitled "SYSTEMS AND METHODS FOR MICROVESSEL ULTRASOUND IMAGING," each of which is herein incorporated by reference in its entirety.

STATEMENT REGARDING FEDERALLY SPONSORED RESEARCH

This invention was made with government support under CA168575, CA195527, EB017213, CA174723, and EB023113 awarded by the National Institutes of Health. The government has certain rights in the invention.

BACKGROUND

To assess and improve the diagnostic performance of non-contrast agent based ultrasound power Doppler imaging, it is essential to have a quantitative measure of image quality. A figure of merit can be useful for quantitative feedback while scanning and as a training tool for operator performance assessment. Further, such a tool is important for power Doppler imaging because despite effective clutter-filtering, even small amount of motion can lead to incoherent integration of the power Doppler ensemble, and produce misleading visualization of microvascular blood flow. Accordingly, a motion corrupted power Doppler ensemble can either result in over-estimation or under-estimation of blood vessels, without any indication or forewarning—especially in the case of small vessel blood flow imaging.

SUMMARY OF THE DISCLOSURE

The present disclosure addresses the aforementioned drawbacks by providing a method for generating an image that depicts microvessels in a subject using an ultrasound system. The method includes providing image data to a computer system. The image data are acquired from a subject with an ultrasound system and comprise image frames obtained at a plurality of different time points. Reformatted data are generated with the computer system by reformatting the image data as a Casorati matrix. Motion matrix data are generated with the computer system by computing a correlation coefficient of each column of the reformatted data with every other column of the reformatted data. The motion matrix data are analyzed with the computer system and based on this analysis updated image data are generated. The updated image data can be generated by directing the ultrasound system to reject image data when analysis of the motion matrix data indicates translation motion occurred when the image data were acquired, by directing the computer system to process the image data to reduce motion corruption when analysis of the motion matrix data indicates periodic motion occurred when the image data were acquired, or both. An image that depicts microvessels in the subject is then generated by reconstructing the image from the updated image data using the computer system.

It is another aspect of the present disclosure to provide a method for generating an image that depicts microvessels in a subject using an ultrasound system. The method includes accessing with a computer system, ultrasound data acquired from a subject with an ultrasound system. The ultrasound data include image frames obtained at a plurality of different time points. Spatiotemporal matrix data are generated with the computer system by reformatting the ultrasound data as a Casorati matrix. Clutter-filtered Doppler ensemble ("CFDE") data are generated with the computer system by inputting the spatiotemporal matrix data to a clutter filter, generating output as the CFDE data. Spatiotemporal correlation data are generated by inputting the CFDE data to a spatiotemporal correlation filter. A synthetic noise image is generated with the computer system based on statistics computed from the spatiotemporal correlation data. Background noise field data are generated from the synthetic noise image using the computer system. A power Doppler image is generated from the CFDE data, and a noise-suppressed power Doppler image is generated with the computer system by normalizing the power Doppler image using the background noise field data, wherein the noise-suppressed power Doppler image depicts microvessels in the subject.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Figure 1:
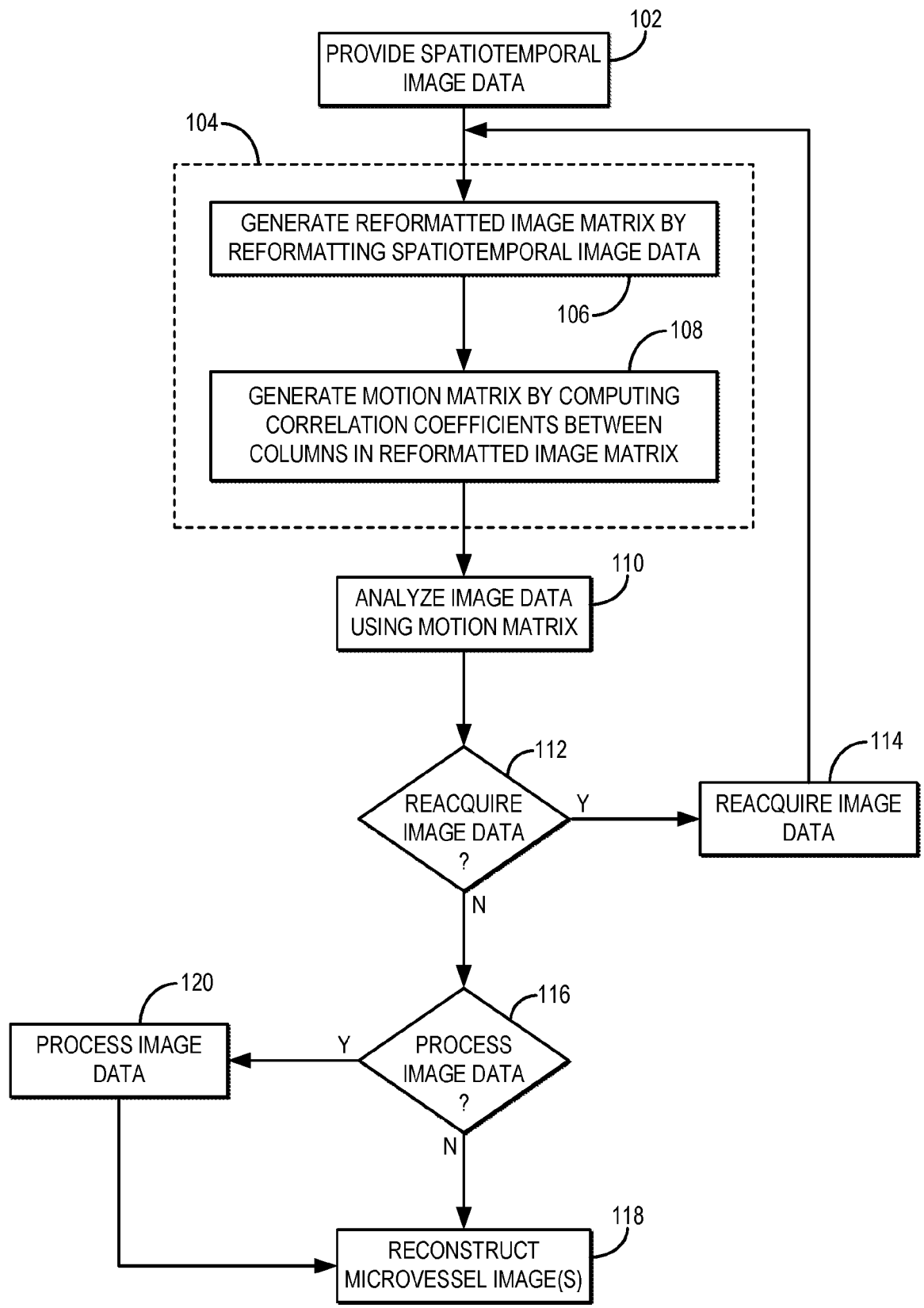
FIG. 1 is a flowchart setting forth the steps of an example method for generating a motion matrix for use as a performance description for non-contrast microvasculature ultrasound imaging.

Described here are systems and methods for generating microvessel images from image data acquired with an ultrasound system. In some aspects of the present disclosure improved ultrasound microvasculature imaging is provided by analyzing the acquired image data in real-time, or retrospectively, to generate a performance descriptor that can be used to assess data quality, motion correction quality, or both. Based on this analysis, it can be determined if the acquired image data is corrupted by motion, frames (e.g., time-points) that need motion correction or rejection can be identified, the quality of different spatial regions in the image data (e.g., spatial points) can be quantified to assess diagnostic confidence, or combinations thereof. Additionally or alternatively, this analysis can be useful in displacement tracking and motion correction in deciding frame-pairs and optimal search window size, which are important parameters for motion tracking; identifying reference frames for motion correction; and quantitatively evaluating the efficacy of motion correction for in vivo patient data.

Additionally or alternatively, it is another aspect of the present disclosure to provide methods for removing background noise in microvessel blood flow images. As an example, the methods can be adaptive and highly efficient, thereby allowing for real-time operation, unlike previous noise suppression and removal techniques, which are performed offline. Advantageously, the methods described in the present disclosure can be combined or implemented separately in order to generate high quality microvessel images.

Additionally or alternatively, it is another aspect of the present disclosure to provide methods for reducing the effects of motion using a non-rigid motion correction.

A motion matrix, as noted above, can be computed based on spatiotemporal similarity between ultrasound data frames that have been reformatted into a Casorati matrix, or the like. This motion matrix indicates coherency of the power Doppler ensemble, and can be estimated in a computationally inexpensive manner. For example, the motion matrix can, in some instances, be computed immediately after data acquisition.

In some instances, the motion matrix can be used to analyze the acquired data in order to determine if the acquired Doppler ensemble is corrupted by motion. The data frames (e.g., time points) that need motion correction or that should be rejected can similarly be identified.

In some other instances, the motion matrix can be used to analyze the acquired data to quantify the quality of different spatial regions in the power Doppler image (e.g., spatial points) to assess the diagnostic confidence of the data.

In still other instances, the motion matrix can be used for displacement tracking and motion correction. For instance, the motion matrix can be used to decide frame-pairs and an optimal search window size, which are important parameters for motion tracking. The motion matrix can also be used to identify a reference frame for motion correction. Moreover, the motion matrix can be used to quantitatively evaluate the efficacy of motion correction for in vivo patient data.

This feedback and assessment measure is important and acutely useful in analyzing in vivo patient data, where any direct comparison with ground truth may not otherwise be clinically feasible.

Using the motion matrix as a quality metric and performance indicator for non-contrast microvasculature ultrasound imaging has a number of advantages. As one example, the motion matrix is easy to compute and is computationally inexpensive. As another example, existing imaging workflows can be readily adapted to include computing and implementing a motion matrix. For instance, the motion matrix can fit into the pipeline of singular value decomposition ("SVD")-based spatiotemporal clutter filtering.

As still another example of an advantage, the motion matrix described in the present disclosure can be useful in obtaining robust feedback on the quality of the acquired data. For instance, the motion matrix can be analyzed to provide feedback to a user (e.g., whether the ensemble should be rejected and reacquired) prior to performing computationally expensive spatiotemporal clutter filtering. As one specific, but non-limiting example, because the SVD-based operation used in SVD-based clutter filtering is not a real-time operation and lacks any quantitative feedback for the acquired data, the pseudo real-time motion matrix can be useful in determining the coherence of the data, which is an important indicator of the quality of the in vivo data.

As still another example, the motion matrix, or other correlated spatiotemporal matrix data, can be used to estimate synthetic noise images, from which a background noise field can be estimated and used for suppressing or otherwise removing noise in microvessel images (e.g., power Doppler images).

Referring now to FIG. 1, a flowchart is illustrated as setting forth the steps of an example method for generating a motion matrix for use as a performance descriptor for non-contrast microvasculature ultrasound imaging. The method includes providing image data to a computer system, as indicated at step 102. The image data may be provided to the computer system by retrieving or otherwise accessing image data from a memory or other data storage device or medium. Additionally or alternatively, the image data may be provided to the computer system by acquiring image data with an ultrasound imaging system and communicating the acquired image data to the computer system, which may form a part of the ultrasound imaging system. In any such instance, the image data are preferably acquired without the use of an ultrasound contrast agent (e.g., a microbubbles-based contrast agent). The image data may be two-dimensional image data or three-dimensional image data. In general, the image data are spatiotemporal data. For instance, the image data may represent a time series of two-dimensional image frames or three-dimensional image volumes.

The image data are then processed to generate a motion matrix, as generally indicated at step 104. The image data are reformatted as a Casorati matrix, or other similar matrix or data structure, as indicated at step 106. For instance, the image data are reformatted as a Casorati matrix by vectorizing each image frame and arranging the vectorized image frames as the columns in the Casorati matrix. In this way, each column of the Casorati matrix corresponds to an image frame obtained from a different time point. The motion matrix is estimated from the Casorati matrix by computing a similarity (or dissimilarity) metric of each column of the Casorati matrix with every other column in the Casorati matrix, as indicated at step 108.

For example, each entry (i, j) of the motion matrix, M, can be computed as a correlation coefficient as follows:

$$M_{i,j} = \frac{\sum_{n=1}^{N} C_i(n) * C_j(n)}{\sqrt{\sum_{n=1}^{N} C_i(n)^2 \sum_{n=1}^{N} C_j(n)^2}}; \quad (1)$$

where $C_i$ and $C_j$ are the (i, j) columns of the Casorati matrix, respectively, and N denotes the number of rows in the Casorati matrix. The entries in the motion matrix will range in values between 0 and 1, where a value of 1 indicates perfect registration between the two images (i.e., the two Casorati columns). In other examples, the similarity metric may be a covariance metric, the angle or magnitude of column vectors in the Casorati matrix, or a distance metric (e.g., Euclidian distance, Manhattan distance, Mahalanobis distance, Minkowski distance). In some instances, the motion matrix is computed from all of the pixels in the image. In some other instances, the motion matrix can be computed from only a subset of the pixels in an image. For example, a local region can be selected and the motion matrix can be computed based on the pixels associated with that local region. The motion matrix can be quantitatively summarized by statistics (e.g., mean, median) to measure performance. Such performance metrics can be provided on a range of 0-1, 0%-100%, or another suitable range.

Because every column of the Casorati matrix represents a vectorized image (e.g., a vectorized 2D image) at a time, t, the normalized correlation of any two columns can quantify the similarity between the two respective images. In the absence of motion, all of the images of the power Doppler ensemble should ideally be the same over the acquisition duration; that is, all columns of the Casorati matrix should be same. In this ideal scenario, the motion matrix would have unitary rank. Consequently, this would lead to very high correlation values in the motion matrix (e.g., values close to 1). However, motion is unavoidable in a clinical setup, whether the motion is caused by physiological sources (e.g., cardiac pulsation), the sonographer's hand motion, the patient's body motion, or so on.

Although some clutter filtering techniques (e.g., SVD-based spatiotemporal clutter filtering) can effectively suppress tissue clutter even in the presence of motion, the lack of image registration will lead to incoherent integration of the power Doppler ensemble. With the help of motion correction, significant gain (e.g., up to 12 dB) in visualization of small vessel signals could be obtained.

Referring again to FIG. 1, after the motion matrix has been generated it can be analyzed to assess the quality of the image data, as indicated at step 110. For instance, the motion matrix can be used as an indicator of the quality of the acquired Doppler ensemble for ultrasound based microvasculature and perfusion imaging. Additionally or alternatively, the motion matrix can be used as an indicator of ensemble coherence. For instance, the mean or median of the motion matrix can be computed and used as a quantitative measure of the coherency of the acquired Doppler ensemble. This can be performed as part of the analysis in step 110 or as a separate step in the process workflow.

As one non-limiting example, the motion matrix can be analyzed to identify image data frames that are associated with translation motion and image data frames that are associated with periodic motion. Knowing whether the underlying motion is translational or periodic is important information that can guide post-processing of the acquired image data. For example, periodic motion is typically physiological motion, which cannot be ignored and should instead be motion-corrected in post-processing. On the other hand, translational motion is typically due to the sonographer's hand motion or due to the patient's body motion. These types of motion indicate that the image data should be reacquired.

Thus, based on the analysis of the motion matrix, a determination can be made at decision block 112 whether some or all of the acquired image data should be reacquired. If so, then the image data are reacquired at step 114 and the reacquired image data are processed at process block 104 to generate a new motion matrix, which is analyzed at step 110.

As another example, based on the analysis of the motion matrix, a determination can be made at decision block 116 whether some or all of the acquired image data should be further processed before reconstructing one or more microvessel images at step 118. If so, this further processing is carried out at step 120 and the one or more microvessel images are reconstructed from the processed image data at step 118. The one or more microvessel images can then be stored for later use or otherwise displayed to as user.

Figures 2A, 2B, 2C, 2D, 2E:
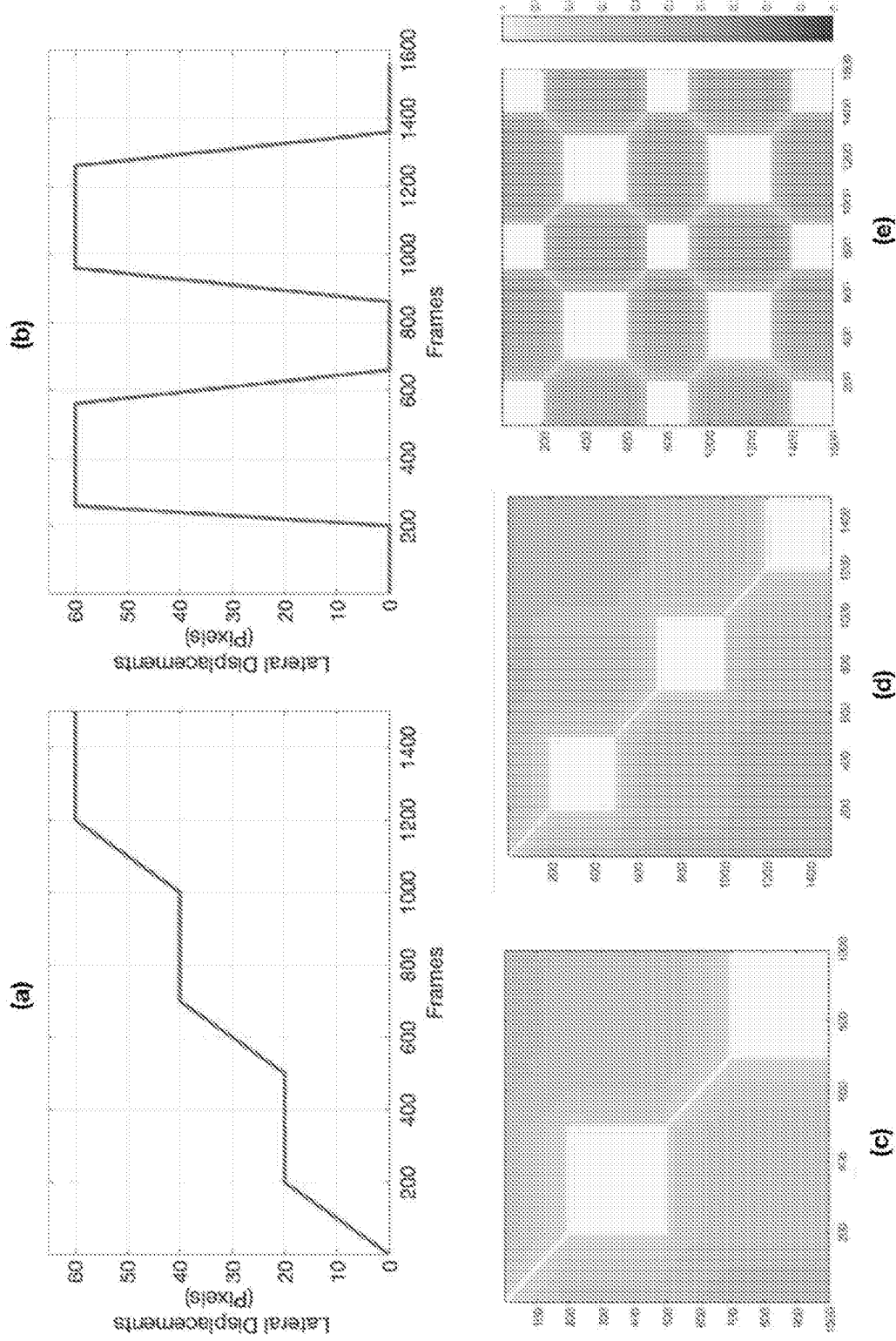
FIGS. 2A-2E show simulated displacements associated with each individual frame of a Doppler ensemble acquired from a tissue mimicking phantom (FIGS. 2A, 2B) and the corresponding motion matrices associated with the spatiotemporal data (FIGS. 2C-2E).

As an illustrative example, FIGS. 2A and 2B display lateral displacements simulated for each IQ frame of a Doppler ensemble. It will be appreciated that although these example simulated displacements were lateral, the methods described in the present disclosure are applicable independent of the direction of motion. Correspondingly, FIGS. 2C and 2D display motion matrices associated with the simulated data from FIG. 2A. Specifically, FIG. 2C represents the motion matrix computed from the first 1000 frames of simulated data and FIG. 2D represents the motion matrix estimated from the entire ensemble of 1500 frames. The results in FIG. 2C show that the frames that encountered motion (e.g., frame numbers 1-200, 500-700, and 1000-1200) had low correlation in the motion matrix and frames with no motion (e.g., frame numbers 200-500, 700-1000, and 1200-1500) displayed high correlation. Accordingly, frames encountering motion can be readily identified from the motion matrix. In addition, the motion matrix can be used as an indicator of ensemble coherence. For instance, the mean or median of the motion matrix can be computed and used as a quantitative measure of the coherency of the acquired Doppler ensemble.

Additionally, it can observed that in the presence of translational motion (e.g., FIG. 2A), off-diagonal patterns were not present in the motion matrices shown in FIGS. 2C and 2D. In the case of periodic motion (e.g., FIG. 2B), off-diagonal entries are observed in the motion matrix (FIG. 2E).

As noted above, knowing whether the underlying motion is translational or periodic is important information that can guide post-processing of the acquired image data.

Figures 3A, 3B, 3C:
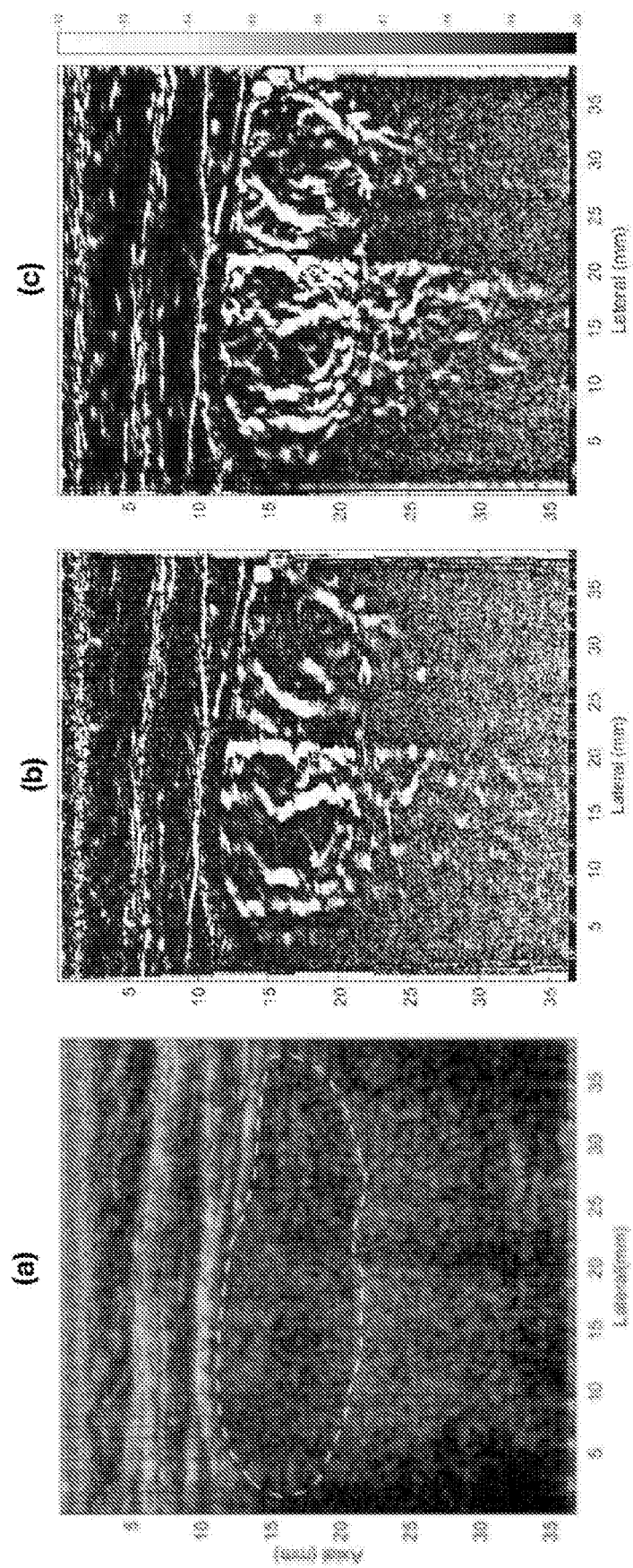
FIGS. 3A-3E show an example of Power Doppler imaging with motion. A B-mode image of a thyroid nodule (FIG. 3A) and the corresponding Power Doppler image are shown without motion correction (FIG. 3B) and with motion correction (FIG. 3C). The corresponding motion matrices before motion correction (FIG. 3D) and after motion correction (FIG. 3E) are also shown.
Figures 3D, 3E:
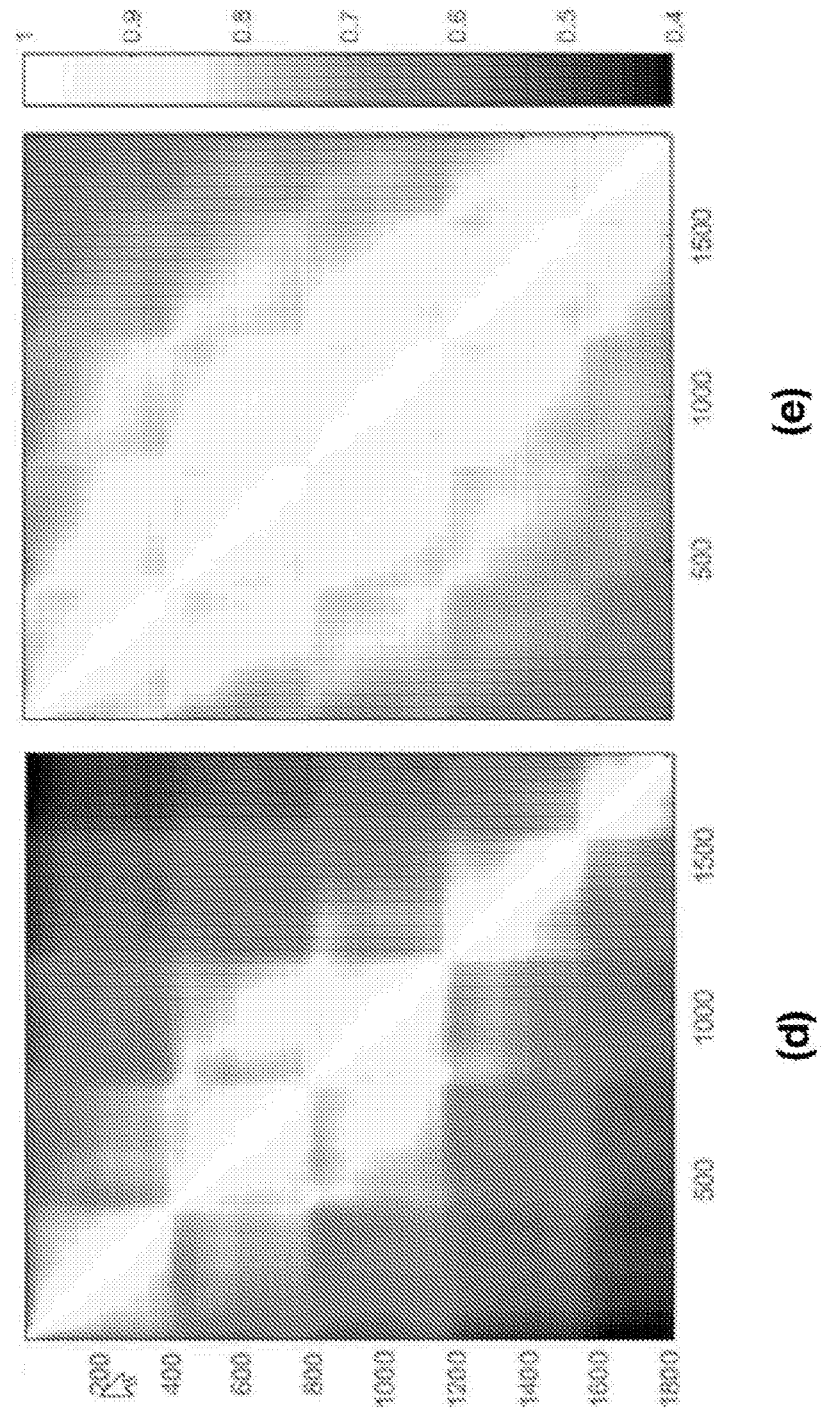

An example role of the motion matrix in the analysis and assessment of in vivo data can be identified in the following examples. FIGS. 3A and 3B display the B-mode and the corresponding power Doppler image of a suspicious thyroid nodule that was under diagnosis for malignancy. It is difficult to identify or quantify any corruption due to of motion from the image in FIG. 3B alone. By analyzing the corresponding motion matrix in FIG. 3D, the lack of spatial coherence can be observed due to the low correlation values. Subsequently, upon motion correction, an improvement in the quality of the power Doppler image (FIG. 3C) and the correlation values in the motion matrix (FIG. 3E) can be observed, which makes the results obtained from the motion corrected data more trustworthy due to its higher coherence.

Figures 4A, 4B, 4C:
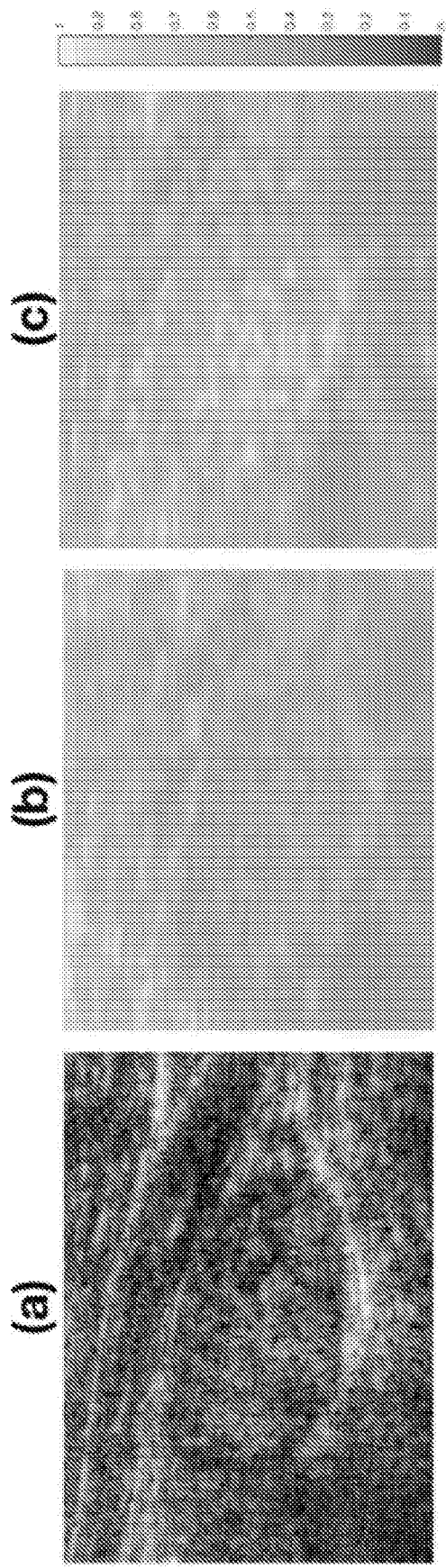
FIG. 4A-4H show a B-mode image (FIG. 4A) of a thyroid nodule; spatiotemporal coherence before and after motion correction (FIGS. 4B, 4C); motion matrices (FIGS. 4D-4E) prior to motion correction (FIG. 4D), after motion correction (FIG. 4E), and after rejection of frames identified to undergo out-of-plane motion (FIG. 4E); and power Doppler maps before motion correction (FIG. 4G) and after motion correction and frame rejection (FIG. 4H).
Figures 4D, 4E, 4F:
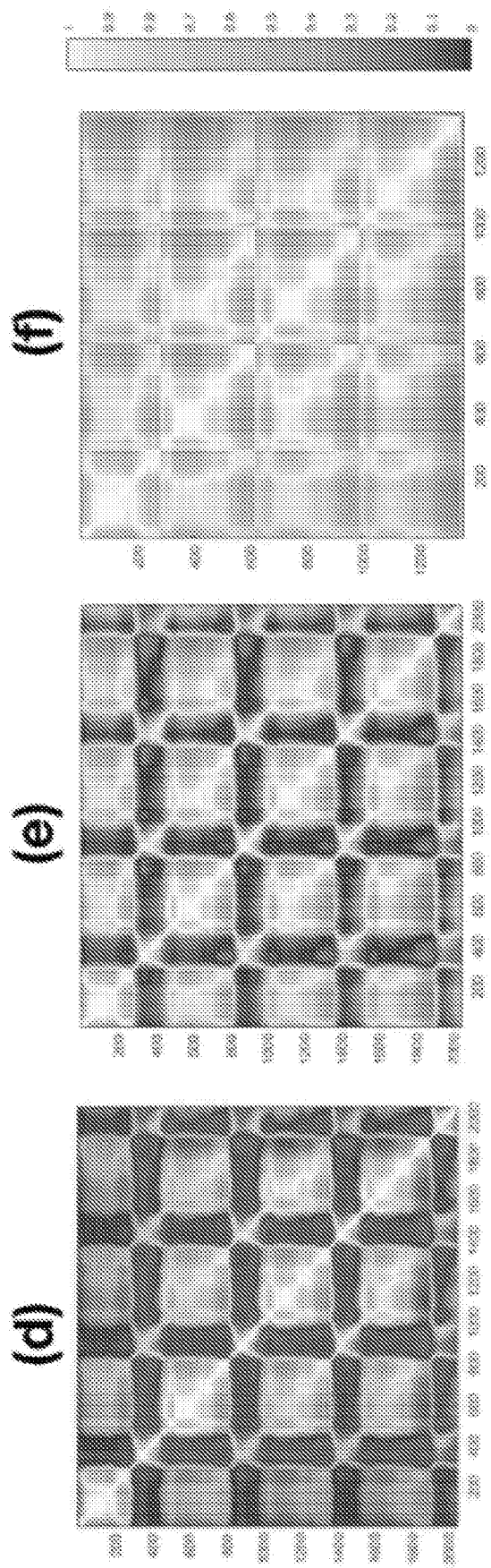
Figure 4G:
Figure 4H:

FIGS. 4A-4H demonstrate the role that the motion matrix can have in assessing the quality of the power Doppler image associated with a suspicious thyroid nodule under diagnostic investigation. Due to the presence of motion, the low coherence in the nodule region is observable in the spatiotemporal coherence map shown in FIG. 4B. After motion correction (FIG. 4C), there was a sharp increase in the correlation values of the motion matrix. The spatiotemporal coherence map is a separate metric compared to the motion matrix. The latter can indicate the quality of the entire ensemble, while the spatiotemporal coherence map can indicate the reliability of each local region in the microvessel image. The spatiotemporal coherence map can be computed by estimating the mean of the motion matrix in an N×N windowed kernel centered at every pixel, representing the spatiotemporal coherence value at that pixel. The corresponding motion matrices obtained from the thyroid nodule region are displayed in FIG. 4D (prior to motion correction), FIG. 4E (post-motion correction), and FIG. 4F (after rejection of frames identified to undergo out-of-plane motion). The final ensemble associated with FIG. 4F can be quantitatively confirmed to be highly trustworthy due to its high mean coherence. The corresponding power Doppler maps associated with FIGS. 4D and 4F are shown in FIGS. 4G and 4H, respectively, which shows improved visibility in the blood flow signal in the thyroid nodule.

Figures 5A, 5B, 5C:
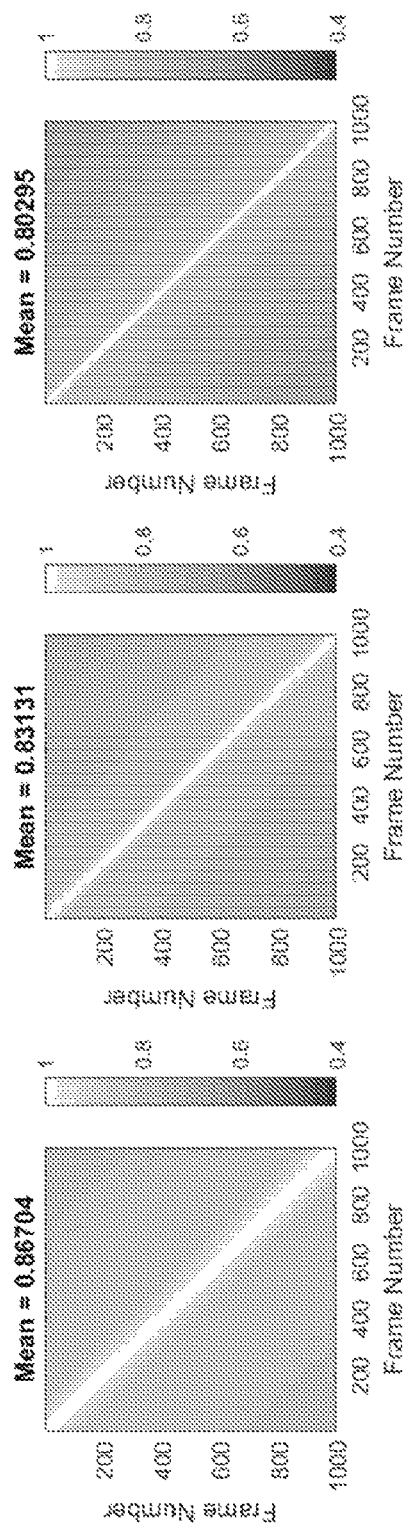
FIGS. 5A-5D display the motion matrix associated with simulated lateral translational motion of 15, 30, and 45 pixels in a homogenous phantom, over an ensemble size of 1000 frames acquired in 3 seconds. The motion matrix associated with the each case displays the corresponding loss in coherence of the Doppler data. The highest coherence was observed in FIG. 5A with the smallest motion, and the lowest coherence was observed in FIG. 5C with the largest motion. Further, the profile of the motion matrix (indicated with colored dashed-lines), for frame number 500, is displayed in FIG. 5D.
Figure 5D:
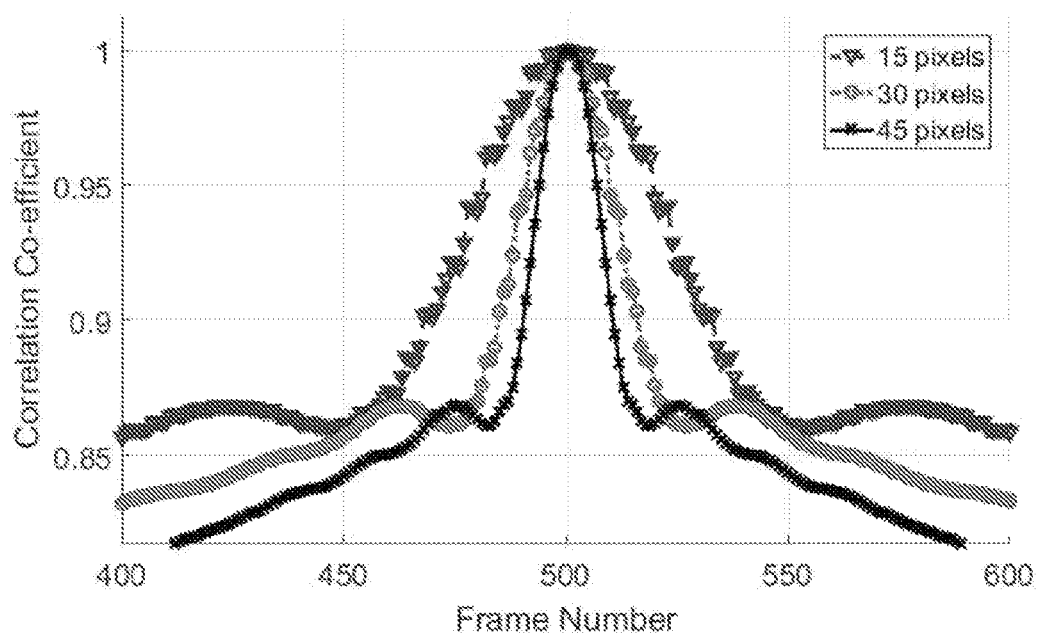

FIGS. 5A-5D display the motion matrix associated with simulated lateral translational motion of 15, 30, and 45 pixels in a homogenous phantom, over an ensemble size of 1000 frames acquired in 3 seconds. The motion matrix associated with the each case displays the corresponding loss in coherence of the Doppler data. The highest coherence was observed in FIG. 5A with the smallest motion, and the lowest coherence was observed in FIG. 5C with the largest motion. Further, the profile of the motion matrix (indicated with colored dashed-lines), for frame number 500, is displayed in FIG. 5D. This information can be useful in identifying the width of the bell shaped curve around frame number 500, which will estimate the maximum frame-skip size suitable for motion tracking. A small or large frame-skip size may be associated with too little motion or too large motion to accurately track, respectively. Therefore, this bell curve can provide a quantitative way to estimate the maximum skip size that can be safely used in choosing frame-pairing for tracking displacements without the pair of frames being totally dissimilar, in which case they cannot be reliably used for tracking. Further, this optimal frame-pairings can be estimated for each frame in the ensemble. More specifically, it can be observed in FIG. 5D that, corresponding to a threshold of 95% similarity, for small motion, a large inter-frame gap can be used for tracking, whereas as for large motion, a smaller inter-frame separation may be more advantageous. In FIG. 5D, the optimal inter-frame separation for the cases in FIGS. SA-SC at 500th frame, to ensure 95% confidence, was observed to be 500±20, 500±12 and 500±7, respectively. This logic also extends to choosing the optimal search kernel size for motion tracking of the ultrasound frames.

Non-invasive, contrast-free imaging of small vessel blood flow is diagnostically invaluable for detection, diagnosis, and monitoring of disease. Recent advances in ultrafast imaging and tissue clutter-filtering have considerably improved the sensitivity of power Doppler ("PD") imaging in detecting small vessel blood flow. Suppression of tissue clutter can, however, expose the depth-dependent time-gain compensated noise bias, which may noticeably degrade the PD image.

Using the methods described in the present disclosure, background suppression of PD images based on a noise bias estimated from the entire clutter-filtered singular value spectrum can considerably improve flow signal visualization compared to currently existing techniques. As described below, the methods described in the present disclosure can advantageously separate the noise and blood flow components, which can otherwise be challenging to reliably separate because they overlap in the singular value spectrum. In general, a spatiotemporal correlation ("STC") filter is used to separate noise and flow components based on a normalized correlation factor.

Figure 6:
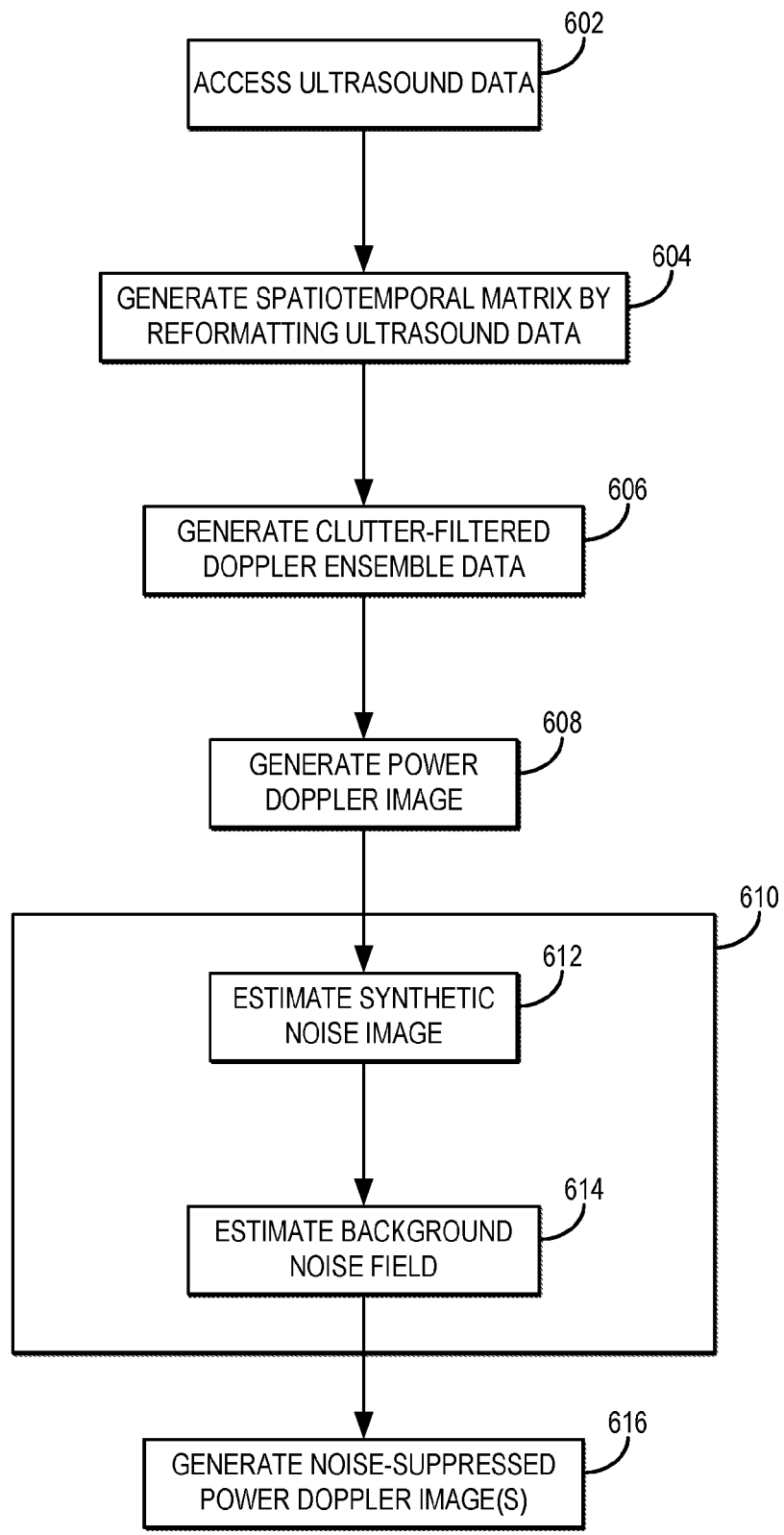
FIG. 6 is a flowchart setting forth the steps of an example method for adaptively suppressing or otherwise removing noise in ultrasound microvessel imaging.

Referring now to FIG. 6, a flowchart is illustrated as setting forth the steps of an example method for adaptively suppressing or otherwise removing noise in ultrasound microvessel imaging, which may be implemented in real-time or retrospectively.

The method includes accessing ultrasound data with a computer system, as indicated at step 602. Accessing ultrasound data can include retrieving previously acquired ultrasound data from a memory or other data storage device or medium. In other instances, the ultrasound data can be accessed by acquiring the ultrasound data with an ultrasound system and communicating, transferring, or otherwise providing the acquired ultrasound data to the computer system. In these instances, the ultrasound data can be provided to the computer system in real-time while the data are being acquired, or after the data have been acquired.

As one non-limiting example, the ultrasound data may be ultrasound in-phase and quadrature ("IQ") data, which may be acquired using plane wave ("PW") or other suitable imaging techniques. For instance, plane wave IQ data can be acquired using a number of different angular insonifications (e.g., −3°, −2°, −1°, 0°, +1°, +2°, +3°), which can then be coherently compounded, such as after delay-and-sum beamforming, to produce a single IQ frame that is dynamically focused on both transmit and receive. The ultrasound data are preferably acquired without the use of an ultrasound contrast agent (e.g., a microbubbles-based contrast agent). The image ultrasound may be two-dimensional image data or three-dimensional image data. In general, the ultrasound data are spatiotemporal data. For instance, the ultrasound data may represent a time series of two-dimensional image frames or three-dimensional image volumes.

The ultrasound data (e.g., high frame-rate compounded plane wave ultrasound images) are rearranged in a spatiotemporal matrix (e.g., a Casorati matrix), as indicated at step 604. Tissue clutter is then suppressed by inputting the spatiotemporal matrix to a singular value decomposition ("SVD"), generating output as clutter-filtered Doppler ensemble ("CFDE") data, as indicated at step 606. For instance, the following SVD can be implemented:

$$S_{blood} = S(x, z, t) - \sum_{r=1}^{r=th} U_r \lambda_r V_r^*; \qquad (2)$$

where the matrices S and $S_{blood}$ represent pre-CFDE and post-CFDE data. The matrices U and V are left and right singular orthonormal vectors, respectively. The corresponding singular values and their orders are denoted by $\lambda_r$ and r, respectively, and "*" represents the conjugate transpose. A global SV threshold (th) for separation of tissue clutter from blood signal can be selected, for example, based on the decay of the double derivative of the singular value orders (i.e., when the double derivative approached zero).

A power Doppler ("PD") image is generated from the CFDE data, as indicated at step 608. For instance, the PD image can be estimated through coherent integration of the CFDE data as follows:

$$PD(x, z) = \sum_{t=1}^{N_t} |S_{blood}(x, z, t)|^2; \qquad (3)$$

where $N_t$ is the ensemble length of the CFDE data.

A background noise field, which will be used to suppress or otherwise remove noise from the PD image, is also estimated from the CFDE data, as indicated at step 610. The background noise field can be estimated in two steps: estimation of a synthetic noise image from the CFDE data, as indicated at process block 612, and estimation of the background noise field from the synthetic noise image based on a low-rank approximation, as indicated at process block 614. As an alternative to deriving the noise field using a low-rank approximation method, the noise field can be derived from the synthetic noise image by computing multiple iterations of the synthetic noise image from the CFDE and subsequently averaging them to generate a smoothed version of the noise field. In this approach, any presence of residual flow signal in the synthetic noise image can coherently cumulate in the second step, which in some instances may lead to inadvertent flow suppression.

As one example, the synthetic noise image can be estimated at process block 612 as follows. A spatiotemporal correlation ("STC") filter can be used to identify the flow pixels in the CFDE data, which are then replaced by randomly selected noise pixels from the local neighborhood, to generate the synthetic noise image. STC-based filtering of the CFDE data can be performed in locally overlapping kernels of dimensions m×n×t pixels in axial, lateral, and temporal directions, respectively. The pixels within the 3D kernel can be arranged in the spatiotemporal matrix (e.g., space-time Casorati form) of dimension s×t, where s=m×n. The normalized correlation matrices M of dimension t×t can be computed:

$$M_{i,j} = \frac{\sum_{n=1}^{N} C_i(n) * C_j(n)}{\sqrt{\sum_{n=1}^{N} C_i(n)^2 \sum_{n=1}^{N} C_j(n)^2}}; \qquad (4)$$

where (i, j) corresponds to each entry in M. Further, $C_i$ and $C_j$ are the (i, j) columns of the spatiotemporal matrix (e.g., Casorati matrix), respectively, and N denotes the number of rows in the spatiotemporal (e.g., Casorati matrix). As described above, these normalized correlation matrices may also be referred to as a motion matrix. Thus, in some instances the synthetic noise image can be computed from a motion matrix, such as the motion matrices computed as described above. The spatiotemporal correlation matrix, M, quantifies the similarity of the pixels in the 3D kernel. Highly dissimilar pixels corresponding to noise will generally yield a low correlation value (e.g., approximately zero), whereas those associated with flow pixels will generally yield a relatively higher correlation value (e.g., greater than 0.4). This information can be used to synthesize a purely noise image as noted above, from which the inherent noise bias can be deduced.

As an example, the synthetic noise image can be estimated based on mean values, or other statistical measures, of the normalized correlation matrices (or motion matrices). For instance, the mean of the estimated correlation matrices, which ranged between 0-1, can constitute the intensity of the pixels in the STC image. Specifically, the pixel intensity at location (x, z) in the STC image can be estimated by computing the mean of the correlation matrix, M, associated with the local kernel centered at (x, z) of the CFDE data.

The correlation values associated with flow pixels are relatively higher compared to noise. Accordingly, they can be separated based on gray-scale thresholding of the STC image. Because noise is expected to be statistically uniform across all columns and frames of the Doppler ensemble, the identified blood flow pixels can be replaced by noise pixels randomly selected from the lateral neighborhood, across multiple frames of the CFDE data.

Further, because the amplification due to time gain compensation ("TGC") varies gradually across depth, the replacement noise pixels can be selected from over a range of depth (e.g., rows), without affecting the performance of the technique. As a non-limiting example, the gray scale threshold can be empirically chosen (e.g., a value of 0.30). Pixels with higher or lower STC values were identified as blood vessel or noise, respectively. The local noise neighborhood can be limited to pixels, across rows, across columns, and across frames, respectively.

As one example, the background noise field can be estimated from a synthetic noise image at process block 614 as follows. The background noise field can be characterized by a smooth depth-increasing signal that is replicated across all columns of the image, consistent with the notion that TGC is applied uniformly across all receive channels. Accordingly, to derive the noise field that is repetitive across all columns of the synthetic noise image, a SVD-based, or other, low-rank matrix approximation can be implemented. For instance, the noise field can be reconstructed using the lowest singular order component that also corresponds to the highest singular value. In instances where the low-rank noise field is estimated from a single synthetic noise image, it may be advantageous to subsequently smooth the estimated noise field, such as by using a two-dimensional ("2D") least squares method that fits a 2D plane in locally overlapping kernels across the depth of the image. As one non-limiting example, the axial and lateral widths of the kernels can be on the order of 100 and 192 pixels, respectively. The kernels can overlap by one or more pixels. As one non-limiting example, the pixels can overlap by one pixel. In some instances, the kernels can also be constrained to have zero-slope in the lateral direction.

Referring still to FIG. 6, a noise-suppressed power Doppler image is generated using the estimated background noise field, as indicated at step 616. For example, a background-suppressed power Doppler image can be computed by normalizing the original power Doppler image using the estimated background noise field. This corresponds to a subtraction of the estimated background noise field from the original power Doppler image in the log scale that is used for image display. Accordingly, total suppression of noise bias can lead to as little as a 0 dB background signal.

Figure 7:
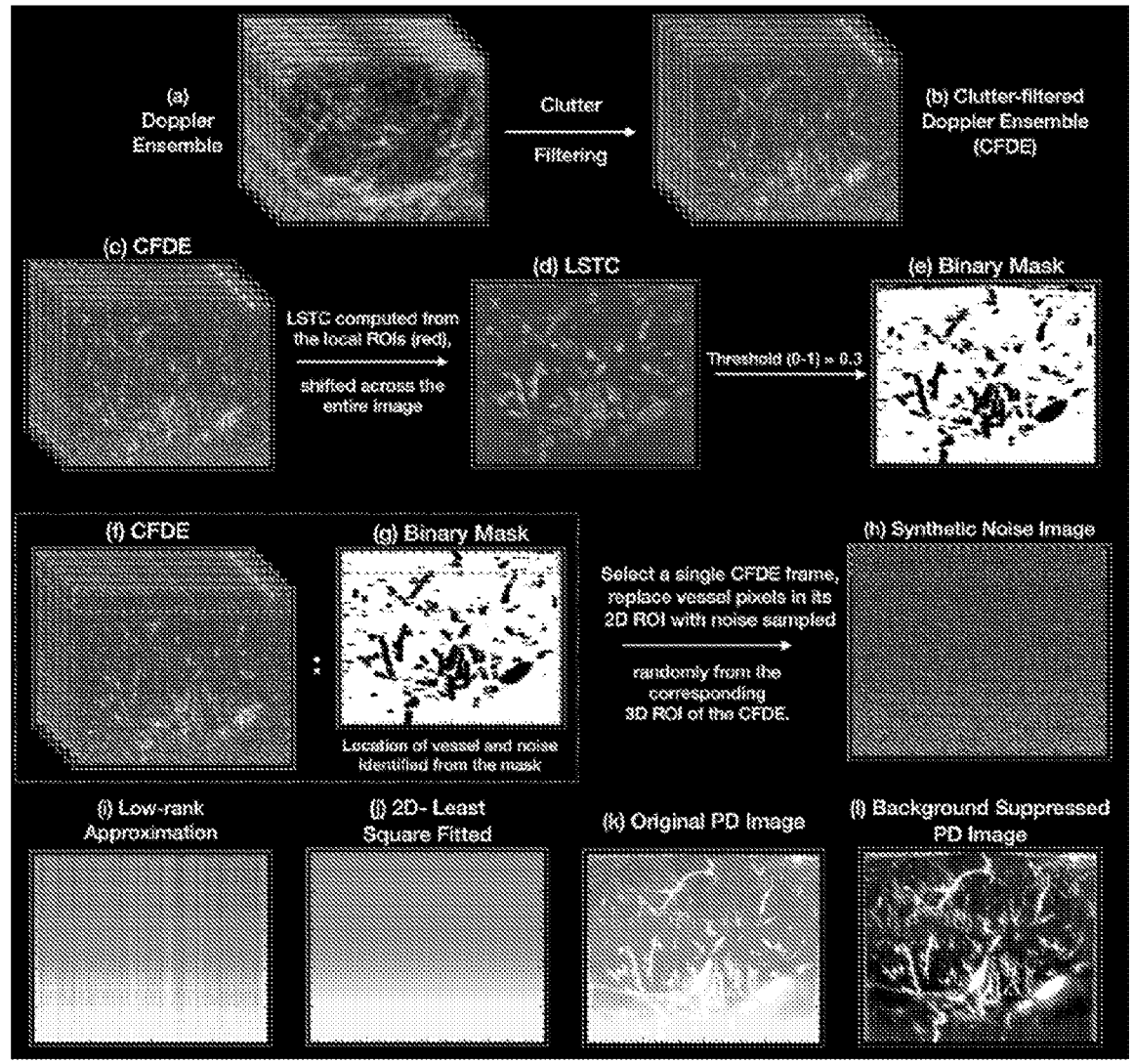
FIG. 7 shows an illustration of the different steps of an example noise-bias suppression algorithm. (a, b) display the acquired Doppler ensemble, and the corresponding clutter-filtered Doppler ensemble (CFDE), respectively. The corresponding LSTC image (d) is computed from the CFDE (c) by estimating spatiotemporal correlation in local 3D kernels (red). (e,g) displays the binary mask computed by greyscale thresholding of the LSTC image, which is inherently normalized between 0-1. The black and white regions corresponds to the location of the flow and noise pixels, respectively. The synthetic noise image (h) is generated from a single clutter filtered image, by replacing its vessel pixels by randomly selected noise from its local 3D neighborhood in the corresponding CFDE (f). (i) displays the low-rank approximation of the synthetic noise image (h), which is subsequently smoothened using a 2D least-square based plane-fit algorithm to generate the final noise field (j). The final PD image (1) is obtained by suppressing the estimated noise field (j) in the original PD image (k).

An illustrative example is shown in FIG. 7 to outline the different steps involved in an example method for estimating a synthetic noise image from the Doppler ensemble. Steps (a, b) display the acquired Doppler ensemble and its corresponding CFDE, respectively. The LSTC image (d) is computed from the CFDE (c) from local estimation of spatiotemporal correlation in 3D kernels (red), as defined in Eqn. (4). Steps (e,g) display the binary mask generated by greyscale thresholding of the LSTC image. Accordingly, the binary black and white regions correspond to the location of the flow and noise pixels, respectively. A single clutter filtered image from (b) is converted into a synthetic noise image (h) by replacing the vessel pixels by noise. The noise pixels are sampled from the entire CFDE; however, from the local neighborhood, representatively indicated by the red 3D kernel in (f). Steps (i,j) display the low-rank approximation of the synthetic noise image, and the corresponding 2D smoothened noise bias image, respectively. The final PD image (l) is obtained by suppressing the estimated noise field (j) in the original PD image (k).

The noise field in the PD image depends on multiple imaging parameters (e.g. TGC, imaging frequency, transmit waveform, etc.). Advantageously, suppression of the noise bias using the methods described in the present disclosure doesn't change the morphological features of the vasculature or the relative intensity of the flow signal with respect to the background. Preserving vascular morphological features is advantageous because they carry important information about disease condition and are useful for robust quantitative assessment of the vasculature.

In the presence of large motion (e.g., physiological motion, motion due to the sonographer's hand motion), tissue frequencies can be similar or even higher than that of slow blood flow. In these instances, the visualization of small vessel blood flow, which can be of low frequency (or velocity) because of small vessel diameter, can be limited. Thus, the presence of tissue motion, physiological motion, or other large motions can impact coherent integration of the power Doppler signal, which can lead to poor visualization of blood flow. Further, the importance of motion correction is not limited to coherent integration of the Doppler ensemble, but can also be used to improve the performance of clutter filtering. Additionally or alternatively, motion correction can be advantageous for low imaging frame-rate applications, such as those due to deep-seated tumors, compounding of plane waves, or when using a 64-channel or other comparable channel system.

It is thus another aspect of the present disclosure to provide methods for mitigating or otherwise reducing the effects of motion (e.g., tissue motion, physiological motion, body motion, other sources of motion) on non-contrast microvasculature ultrasound imaging. Previous motion correction techniques made use of a rigid body motion assumption, which has limitations and disadvantages. For instance, the average displacements used for global motion correction is estimated from the lesion area. Accordingly, depending on the outline of the lesion, which is generally subjective, the performance of motion correction can be sub-optimal. Further, in such approaches motion correction is primarily targeted to the vessels in the lesion area, and thus visualization of peri-lesion vascularity may not be optimal.

Another drawback of assuming rigid body motion is that the efficacy of motion correction will be dependent on the variance of the displacement estimates. If the variance (or gradient) is high (i.e., strain is high), then the notion of using average displacement may not be suitable for motion correction. Specifically, applicability of rigid body based motion correction can often be limited to translational motion. For example, for a large lesion under high strain, it is possible that none of the region may be successfully motion corrected due to high deviations of local displacement estimates from the local mean.

Another drawback of assuming rigid body motion is that the presence of out-of-plane motion at local regions between the consecutive frames may necessitate rejection of the entire frame, which can further penalize the quality of the microvascular imaging.

Thus, it is an aspect of the present disclosure to provide non-rigid body motion correction techniques. The systems and methods described in the present disclosure implement a non-rigid body motion estimation and correction that doesn't require a regularization factor and that operates without constrains on smoothness or continuity in tissue behavior upon being subjected to motion. For instance, the non-rigid motion correction implements a localized, blockwise motion tracking and correction to achieve non-rigid correction. Motion between two subsequent frames can be estimated in local kernels using 2D normalized cross-correlation. Subsequently, the motion can be corrected locally. The size of the kernels can be varied based on the variance of displacements in the kernel in order to achieve uniform displacements (e.g., zero Cartesian strain) to perform a local rigid-body based translational correction.

The non-rigid motion correction techniques described in the present disclosure provide several advantages. As one example, robust motion correction can be performed even when the lesion or surrounding tissue undergoes strain, which undermines the assumption of purely translational motion that has been primarily used in global motion correction studies. As another example, local frame-rejection criteria can be enforced without having to discard the entire frame. This is advantageous when implementing performance descriptors and outlier rejection, such as those described above, which can influence the quality of the data. As still another example, noise suppression can be improved by using overlapping local kernels.

The non-rigid motion correction techniques described in the present disclosure can also improve the performance of clutter suppression, which is advantageous for visualization of blood flow imaging. For instance, motion correction and clutter suppression can be performed subsequently, which can significantly benefit the efficacy of tissue clutter rejection. Further, because motion correction is performed in small local regions, compared to the entire frame, the systems and methods described in the present disclosure can enable low computational overheads, while each local region can be motion corrected in parallel.

Figure 8:
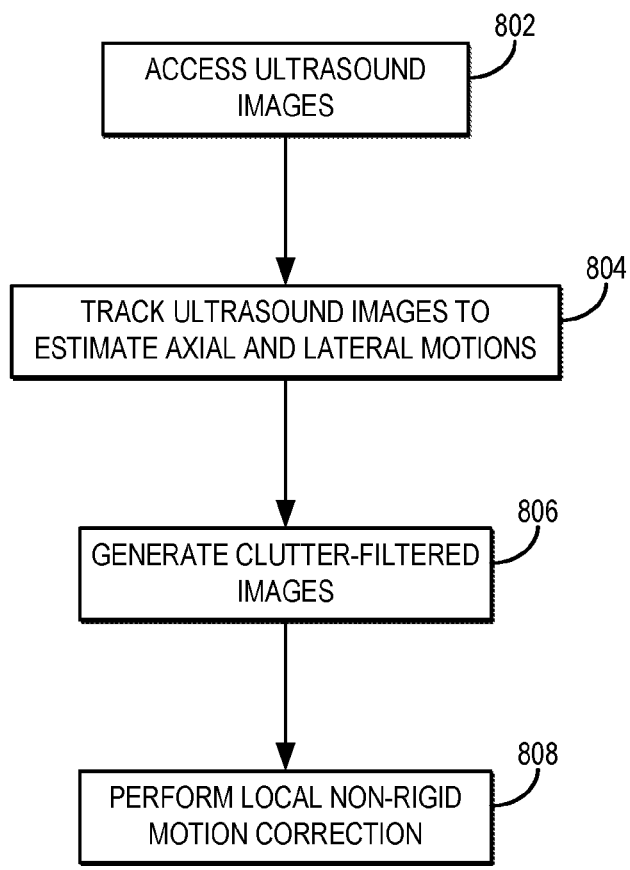
FIG. 8 is a flowchart setting forth the steps of an example method for performing non-rigid motion correction.

Referring now to FIG. 8, a flowchart is illustrated as setting forth the steps of an example method for performing non-rigid motion correction on ultrasound data. The method includes accessing ultrasound images with a computer system, as indicated at step 802. For instance, the ultrasound images may include ultrasound images of a specific region-of-interest ("ROI"), such as a cross-section of a tumor (e.g., in breast, thyroid, lymph node) or an organ (e.g., kidney, liver). The images could be acquired using plane wave or compounded plane wave imaging or virtual source based multi-element synthetic aperture imaging or synthetic aperture imaging or conventional plane wave imaging or multi-plane wave imaging or other similar imaging approaches. Accessing the ultrasound images can include retrieving previously acquired ultrasound images from a memory or other data storage device or medium. Alternatively, accessing the ultrasound images can include acquiring the images using an ultrasound system and communicating or otherwise transferring the images to the computer system, which may be a part of the ultrasound system.

The ultrasound images are then tracked to estimate the axial and lateral motion associated with the ROI, as indicated at step 804. For instance, the ultrasound images can be tracked using 2D displacement tracking techniques to estimate the axial and lateral motion associated with the ROI, which could be due to motion due to physiological motion, breathing, sonographer's hand motion, patient's body motion, or some combination thereof. The displacements associated with every pixel can be estimated by any number of suitable displacement tracking techniques, including two-dimensional normalized cross-correlation based tracking or dynamic programming, global ultrasound elastography (GLUE), and so on. The axial and lateral displacements associated with every pixel (local region) obtained in this step will be utilized for motion correction, which can advantageously support coherent integration of the Doppler ensemble. At step 804, displacement tracking can also be performed using the tissue data that are typically rejected from the Doppler ensemble, to ensure that the decorrelation of ultrasound speckle due to noise and presence of blood signal is minimized.

The ultrasound images are also processed for suppression of tissue clutter, as indicated at step 806. For example, tissue clutter is 100 dB greater than that of the signal from blood, and it can significantly obscure the visualization of blood flow. Tissue can be suppressed using any number of suitable techniques, such as (i) high pass spectral filtering, (ii) spatiotemporal clutter filtering using singular value decomposition, or (iii) tissue clutter filtering using independent component analysis. Furthermore, clutter suppression can be performed globally (using the entire frame) or locally (using local regions of the frame to determine the filtering parameters exclusively with respect to the speckle properties in that local region.) It will be appreciated that steps 804 and 806 can be performed serially or in parallel, with the latter approach reducing overall processing time.

The clutter-filtered images are corrected for motion using the local displacements obtained from step 804, as indicated at step 808. For non-rigid body based local motion correction, a local region of a predefined size (fixed or variable across the image), of rectangular, square or polygonal span along the spatial dimensions is considered for all time points. The Cartesian displacements (axial and lateral) averaged over the local region, which can be expected to be more uniform than a global estimate, can be used for motion correction. Motion correction of the Doppler ensemble can be performed to re-register each ultrasound frame with that of the first frame, by shifting the rows and columns by the estimated displacements. In these instances, the mean axial and lateral displacements obtained from local ROI of each frame can be used to correct for motion.

To reduce memory overload, the motion corrected ensemble can be stored as a local power Doppler image, corresponding to that ROI. For instance, the local power Doppler image can be computed by estimating the mean square value of each pixel in time.

The local, non-rigid motion correction process described above is repeated for other ROIs in the image, which may have a spatial overlap with neighboring ROIs. Pixels that belong to multiple ROIs due to spatial overlapping will accordingly have multiple power Doppler intensities, which can be averaged with respect to the counts of overlaps. The amount of overlap between ROIs can be adjusted by the user. In general, increasing the amount of overlap will increase computation time. Increasing the amount of overlap will also increase the averaging that occurs in the overlapping ROIs, which in turn reduces noise (i.e., if a pixel is included in N overlapping ROIs, then corresponding to each ROI it will have a motion corrected PD intensity value, and altogether a total of N PD values). Averaging of data in the overlapping ROIs can significantly reduce noise and increase the visualization of the micro vessel blood flow signal.

The non-rigid motion correction techniques described above can also be adapted for local clutter suppression techniques. For example, clutter suppression in local regions can be improved by motion correction of the Doppler ensemble. Further, from the point-of-view of coherent integration of the Doppler signal, locally clutter-filtered data can be motion corrected to ensure coherent power Doppler integration, which is advantageous for reliable visualization of the blood vessels.

As described above, performance descriptors can also play an important role in microvasculature imaging. Performance descriptors, such as local spatiotemporal coherence matrices (e.g., motion matrices as described above) and images can be useful in identifying local regions that need motion correction. Thus, in some implementations, only those regions identified as having low spatiotemporal coherence may be selected for local motion tracking and correction. Further, a spatiotemporal coherence matrix (e.g., motion matrices as described above) can be used to identify frames that should be motion corrected or rejected. This approach can significantly reduce the computational burden associated with motion tracking and correction, which is advantageous for real-time imaging.

A spatiotemporal coherence matrix-based performance descriptor can also be useful in assessing the performance of motion correction, and identifying frames that weren't successfully motion corrected and thus can be a candidate for rejection. Compared to the global approach in which the entire frame must be rejected, in the local approach the frame rejection criteria can be limited to local regions that can be helpful in maximizing the contribution from the coherent data, while selectively rejecting data corresponding to incoherent regions.

Figure 9:
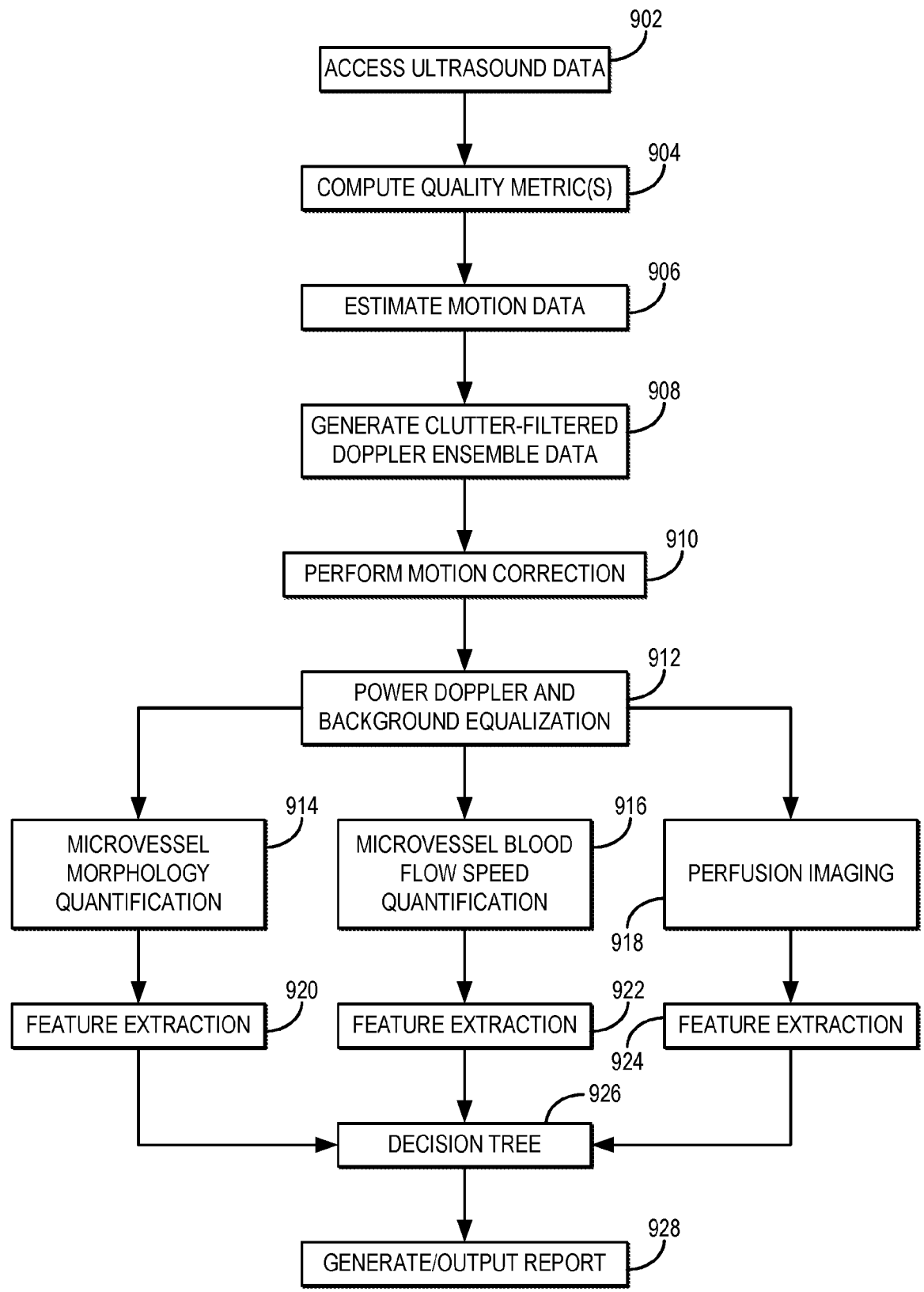
FIG. 9 is a flowchart setting forth the steps of an example method for assessing intraventricular hemorrhage risk in neonates using the systems and methods described in the present disclosure.

Referring now to FIG. 9, a flowchart is illustrated as setting forth the steps of an example method for predicting or otherwise assessing the likelihood of intraventricular hemorrhage in a subject, such as a neonatal subject, based on non-contrast ultrasound microvessel imaging.

The method includes acquiring ultrasound images from the subject, as indicated at step 902. The images may be acquired from a specific cross-section (e.g., coronal plane, sagittal plane) of the neonatal brain, through the anterior fontanelle. The images can be acquired using plane wave imaging, multiplane wave imaging, compounded plane wave imaging, virtual source-based multi-element synthetic aperture imaging, synthetic aperture imaging, or other suitable ultrasound imaging approaches.

The data quality of the acquired images can then be assessed based on computing one or more quality metrics, as indicated at step 904. For instance, the methods described above can be implemented to assess the data quality. As an example, a quality check of the Doppler ensemble can be performed on the data acquired using spatio-temporal correlation maps and images. The quality check can also be used for identifying a reference frame for motion correction and assessing the quality of the motion correction, as described above. The quality check can also be useful to determine if the acquired data are suitable for further processing or if they should be discarded and new data should be reacquired.

Motion (e.g., lateral and axial motion) in the ultrasound data can be estimated, as indicated at step 906. As one example, the acquired ultrasound images can be tracked using 2D displacement tracking techniques to estimate the axial and lateral motion associated with the brain tissue, which could be due to motion from the ventilator, breathing, sonographer's hand motion, or due to neonatal head motion. The displacements can be estimated by a number of suitable displacement tracking techniques, including two-dimensional normalized cross-correlation based tracking or dynamic programming, global ultrasound elastography ("GLUE"), and so on. The axial and lateral displacements associated with every pixel (i.e., local region) obtained in this step can be utilized for motion correction, which can be advantageous for coherent integration of the Doppler ensemble.

Clutter-filtered Doppler ensemble data are generated as indicated at step 908. Tissue clutter is generally 100 dB greater than that of the signal from blood, and it can completely obscure the visualization of blood flow. Tissue can be suppressed using a number of suitable techniques, including high pass spectral filtering, spatiotemporal clutter filtering using singular value decomposition, or tissue clutter filtering using independent component analysis. Further, clutter suppression can be performed globally (i.e., using the entire frame) or locally (e.g., using local regions of the frame to determine the filtering parameters exclusively with respect to the speckle properties in that local region.) Steps 906 and 908 both use the same input images, and can be conducted in parallel in order to reduce processing time.

The clutter filtered images can be corrected for motion using the local displacements estimated in step 906, as indicated at step 910. Motion correction can be performed either using a rigid body or non-rigid body based image registration technique, such as those techniques described above. In some implementations, motion correction (rigid or non-rigid) can also be performed prior to clutter filtering. This can be useful in improving the performance of clutter filtering.

The clutter-filtered Doppler ensemble data are coherently integrated to estimate the Doppler ensemble, as indicated at step 912. The estimated microvasculature image will have high time gain compensation based noise bias that can substantially impact the visualization of the microvasculature in the GM, which is the primal spot for hemorrhages in pre-term intraventricular hemorrhage. This background noise can be suppressed using various techniques, including those described above. TGC background noise equalized microvasculature images obtained from step 912 can be used for quantification of vascular features.

As indicated at step 914, in one example microvessel morphology can be quantified. In general, vessel quantification can be performed by converting the microvasculature image to grayscale, followed by automatic segmentation to convert it to a binary image, which will identify blood vessel pixels as ones and background pixels are zeros, or vice versa. Each microvessel in the binary image can be independently identified (e.g., as a blob using a connected component labelling technique). For each microvessel, now identified as an individual group of connected pixels (e.g., a blob) in the binary image, its diameter, length, tortuosity, area, and other such morphological parameters and features can be estimated, which can be used to estimate vascular density in the germinal matrix area identified either from the sonogram or the microvasculature power Doppler image. The morphological vessel parameters can be useful in assessing the distribution of the brain vasculature, which is a relevant indicator of the maturity and strength of the blood vessels and its susceptibility to rupture and hemorrhage.

As indicated at step 916, in another example microvessel flow speed can be quantified. For instance, the speed of blood flow in the brain vasculature can be assessed by calculating the flow speed from the Doppler shift of the received echoes. Quantification of blood flow related parameters can be advantageous in assessing the nature of the flow (e.g., laminar or turbulent), which can be a relevant parameter for assessing the risk of hemorrhage of vessels.

As indicated at step 918, in another example the output of step 912 can also be used for the assessment of functional imaging parameters, such as rate of change in flow volume over time (i.e., tracking the increase or decrease in flow volume in a measured amount of time). This can be used in assessing the stability of blood flow in adjoining brain regions (to the susceptible germinal matrix) such as the gray matter, white matter, cortex, and so on.

Features are extracted from these different quantitative parameter sets or maps, as indicated at step 920, 922, and 924, and fed individually, all together, or in other combinations to a multi-parameter decision and estimation tree algorithm, as indicated at step 926, in order to determine if the microvessels in the brain's germinal matrix are susceptible to rupture. As an example, the decision tree algorithm can implement a neural network, a least square based estimator, a Bayesian estimator, a Kalman filter, and so on. The microvessel morphology can be useful in assessing the maturity and integrity of the blood vessels in the germinal matrix. The microvessel blood flow parameters can be useful in assessing the hemodynamics of the blood flow, which is a relevant factor that governs risk of rupture of GM vasculature.

As indicated at step 928, the decision tree algorithm generates output, which may be a report indicating a risk of intraventricular hemorrhage. The report can include images, quantitative parameters (e.g., probability scores), textual data, or combinations thereof. For instance, the report can include a feature map or probability map that indicates a risk of IVH at spatial locations within the subject's brain. As another example, the report can include one or more scores (e.g., a probabilistic score) that indicates a risk of IVH in the subject. These output data can be stored for later use or presented to a user, such as by displaying the report on a display, which may include generating a graphical user interface that presents the report to a user.

The systems and methods described in the present disclosure provide for cerebrovascular acoustography ("CEVA") that can measure cerebral blood flow fluctuations in the germinal matrix and simultaneously quantify the fragility of the germinal matrix vasculature based on pre-established morphological features (e.g., increased vascular density and tortuosity) across the two-dimensional imaging plane in high spatial (e.g., less than 100 micrometers) and temporal (e.g., less than one millisecond) resolution. In one aspect, CEVA measurements of germinal matrix vasculature can be used to robustly predict the risk and severity of IVH. In some implementations, a bed-side ultrasound imaging tool can be used to provide the CEVA measurements and to accurately characterize vascular anatomy and constituent flow fluctuations, robust to motion. As noted, CEVA can also characterize morphologic and hemodynamic parameters in high spatial and temporal resolution across the whole imaging plane.

As one non-limiting example, CEVA can involve acquisition of trans-cranial IQ data using a linear-array US transducer at a frame-rate in sub-KHz, dependent on depth of imaging. Compounded plane wave ("CPW") transmission can also be used to achieve dynamic focusing in both transmit and receive. Imaging of high-resolution vascular features is highly sensitive to motion; thus, the multi-resolution motion tracking and correction techniques described above, which significantly improve the performance of microvascular imaging, can be used. The tissue motion estimated from the US images accurately track and correct in-plane motions up to sub-pixel resolution. The techniques described in the present disclosure can significantly improve the covariance of the spatiotemporal matrix and reduce the rank of the tissue components, thereby allowing more effective clutter-filtering and robust visualization of small vessel signals. Tissue noise that emanates from time gain compensation of US signal can also be suppressed without impacting the morphological or hemodynamic characteristics of flow signal. Vessel morphology can be quantified to estimate vascular density and vessel tortuosity. For instance, morphological quantification can be used to assess tortuosity based on a sum of angles of individual vessel segments. The total number of vessels segments can also be quantified for assessing vascular density, which are important characteristics of germinal matrix vasculature for the assessment of IVH risk.

In some implementations, intra-cycle fluctuations in blood flow can be quantified between the intensity of the flow signal in the systolic and diastolic phases. These intra-cycle fluctuations in CBF can be evaluated to assess risk of IVH. Using the systems and methods described in the present disclosure, CBF fluctuations in the local regions of germinal matrix, in combination with quantitative estimates of vessel fragility (based on vessel morphology) can be estimated. Further, as the full Doppler flow spectrum can be estimated from the high frame-rate ensemble, the traditional flow indices of pulsatility (PI) and flow resistivity (RI) can also be computed, which can give further quantitative insight on germinal matrix flow hemodynamics.

Figure 10:
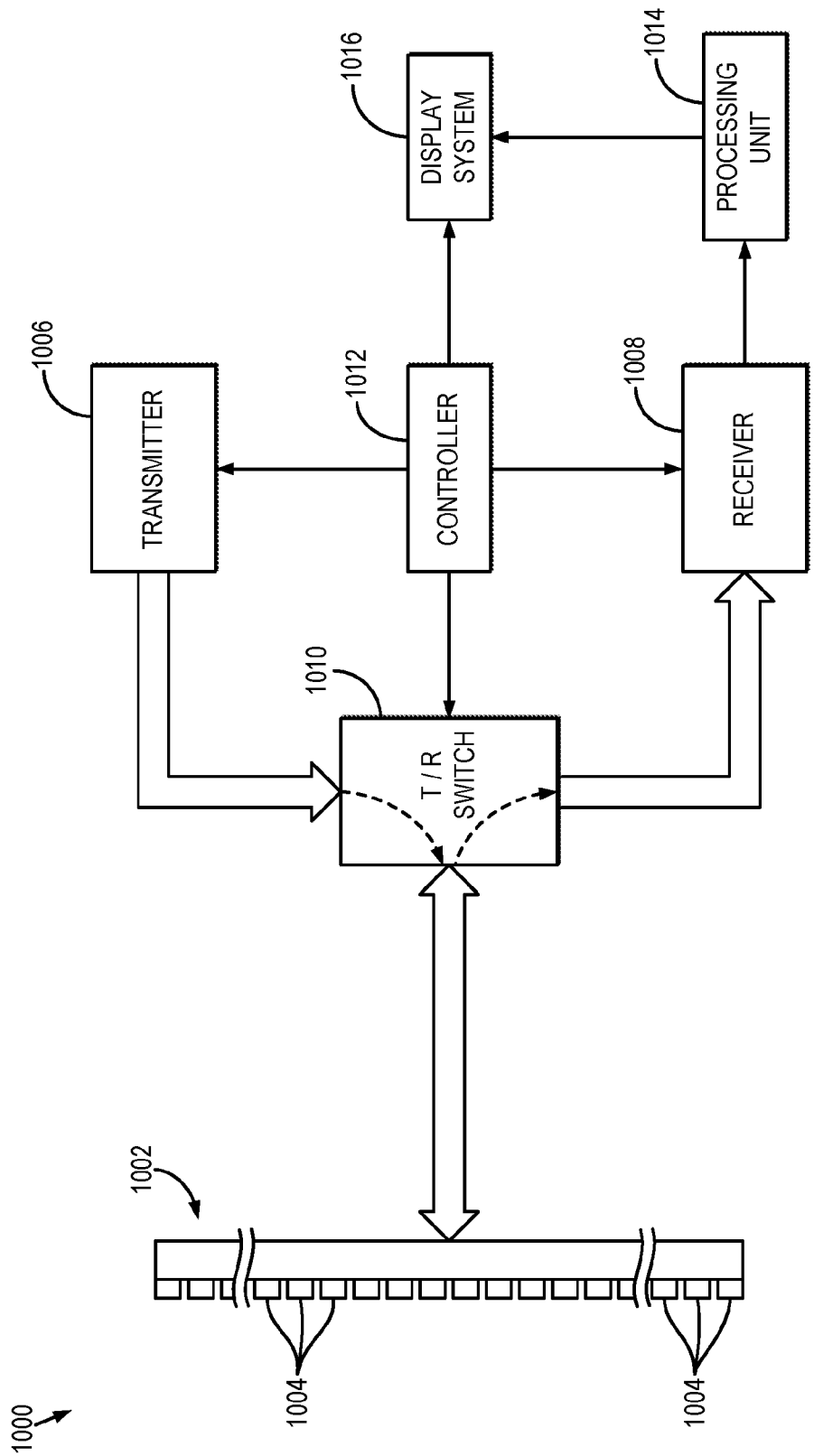
FIG. 10 is an example of an ultrasound system that can be implemented with the systems and methods described in the present disclosure.

FIG. 10 illustrates an example of an ultrasound system 1000 that can implement the methods described in the present disclosure. The ultrasound system 1000 includes a transducer array 1002 that includes a plurality of separately driven transducer elements 1004. The transducer array 1002 can include any suitable ultrasound transducer array, including linear arrays, curved arrays, phased arrays, and so on. Similarly, the transducer array 1002 can include a 1D transducer, a 1.5D transducer, a 1.75D transducer, a 2D transducer, a 3D transducer, and so on.

When energized by a transmitter 1006, a given transducer element 1004 produces a burst of ultrasonic energy. The ultrasonic energy reflected back to the transducer array 1002 (e.g., an echo) from the object or subject under study is converted to an electrical signal (e.g., an echo signal) by each transducer element 1004 and can be applied separately to a receiver 1008 through a set of switches 1010. The transmitter 1006, receiver 1008, and switches 1010 are operated under the control of a controller 1012, which may include one or more processors. As one example, the controller 1012 can include a computer system.

The transmitter 1006 can be programmed to transmit unfocused or focused ultrasound waves. In some configurations, the transmitter 1006 can also be programmed to transmit diverged waves, spherical waves, cylindrical waves, plane waves, or combinations thereof. Furthermore, the transmitter 1006 can be programmed to transmit spatially or temporally encoded pulses.

The receiver 1008 can be programmed to implement a suitable detection sequence for the imaging task at hand. In some embodiments, the detection sequence can include one or more of line-by-line scanning, compounding plane wave imaging, synthetic aperture imaging, and compounding diverging beam imaging.

In some configurations, the transmitter 1006 and the receiver 1008 can be programmed to implement a high frame rate. For instance, a frame rate associated with an acquisition pulse repetition frequency ("PRF") of at least 100 Hz can be implemented. In some configurations, the ultrasound system 1000 can sample and store at least one hundred ensembles of echo signals in the temporal direction. The controller 1012 can be programmed to implement an imaging sequence to acquire ultrasound data. In some embodiments, the controller 1012 receives user inputs defining various factors used in the imaging sequence.

A scan can be performed by setting the switches 1010 to their transmit position, thereby directing the transmitter 1006 to be turned on momentarily to energize transducer elements 1004 during a single transmission event according to the imaging sequence. The switches 1010 can then be set to their receive position and the subsequent echo signals produced by the transducer elements 1004 in response to one or more detected echoes are measured and applied to the receiver 1008. The separate echo signals from the transducer elements 1004 can be combined in the receiver 1008 to produce a single echo signal.

The echo signals are communicated to a processing unit 1014, which may be implemented by a hardware processor and memory, to process echo signals or images generated from echo signals. As an example, the processing unit 1014 can process image data to analyze and assess the quality and ensemble coherence of the image data using the methods described in the present disclosure. In response to this analysis, the processing unit 1014 can direct and implement further processing of the image data, reconstruction of the image data to generate microvessel images, reacquisition of image data when image data are deemed unreliable, computation of one or more quality metrics (e.g., measures of ensemble coherency), and combinations thereof. Images produced from the echo signals by the processing unit 1014 can be displayed on a display system 1016.

Figure 11:
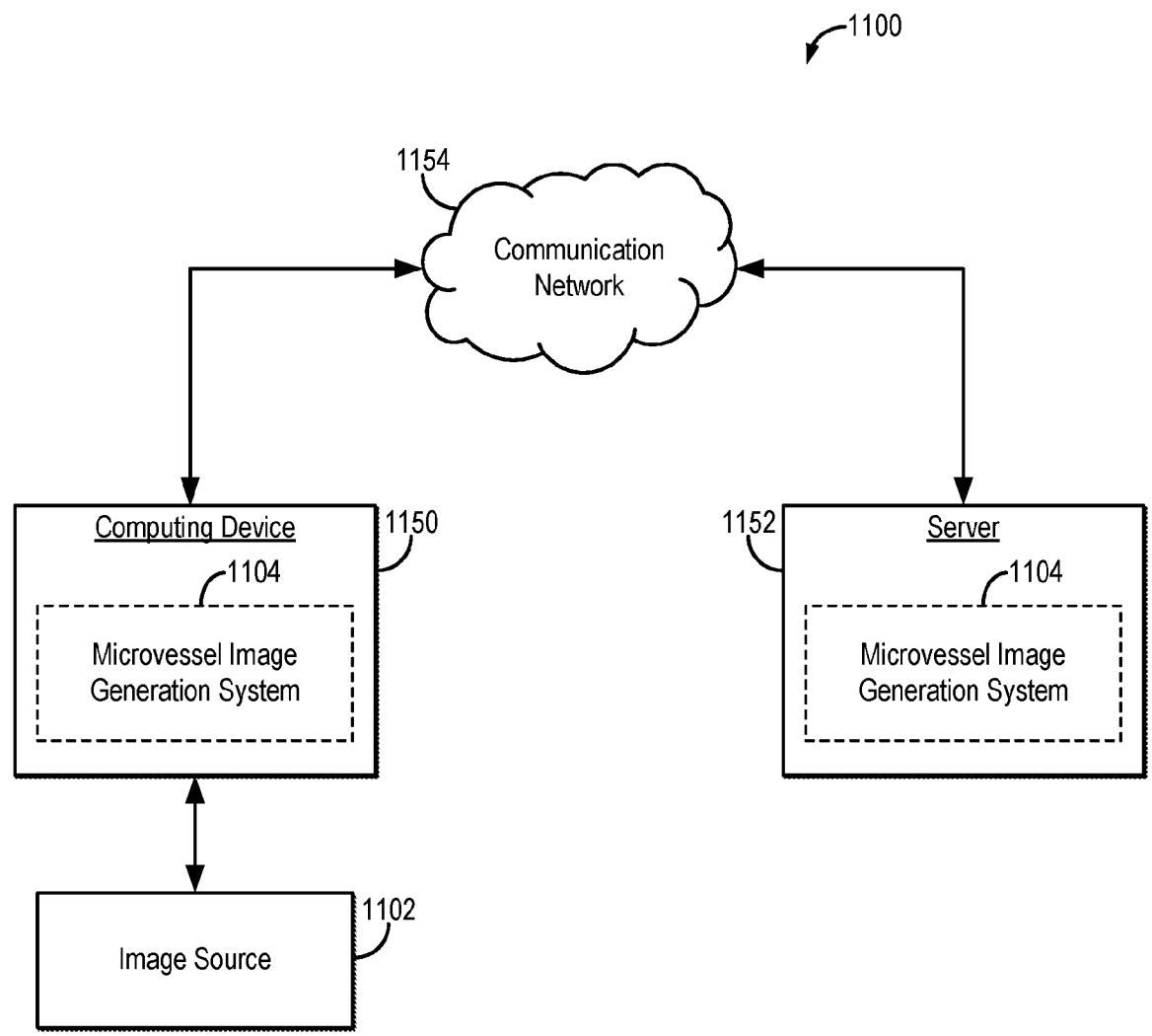
FIG. 11 is a block diagram of an example of a microvessel image generation system.

Referring now to FIG. 11, an example of a system 1100 for generating microvessel images (e.g., microvessel blood flow images) in accordance with some embodiments of the systems and methods described in the present disclosure is shown. As shown in FIG. 11, a computing device 1150 can receive one or more types of data (e.g., ultrasound data) from image source 1102, which may be an ultrasound image source. In some embodiments, computing device 1150 can execute at least a portion of a microvessel image generation system 1104 to generate microvessel images from data received from the image source 1102. As described above, the microvessel image generation system 1104 can implement a performance description system for assessing data quality, motion correlation quality, or both, and for updating ultrasound data based on that performance description. The microvessel image generation system 1104 can also implement an adaptive noise suppression system for suppressing or otherwise removing noise from the microvessel images. In still other examples, the microvessel image generation system 1104 can implement both the performance description and adaptive noise suppression systems described in the present disclosure.

Additionally or alternatively, in some embodiments, the computing device 1150 can communicate information about data received from the image source 1102 to a server 1152 over a communication network 1154, which can execute at least a portion of the microvessel image generation system 1104. In such embodiments, the server 1152 can return information to the computing device 1150 (and/or any other suitable computing device) indicative of an output of the microvessel image generation system 1104.

In some embodiments, computing device 1150 and/or server 1152 can be any suitable computing device or combination of devices, such as a desktop computer, a laptop computer, a smartphone, a tablet computer, a wearable computer, a server computer, a virtual machine being executed by a physical computing device, and so on. The computing device 1150 and/or server 1152 can also reconstruct images from the data.

In some embodiments, image source 1102 can be any suitable source of image data (e.g., measurement data, images reconstructed from measurement data), such as an ultrasound imaging system, another computing device (e.g., a server storing image data), and so on. In some embodiments, image source 1102 can be local to computing device 1150. For example, image source 1102 can be incorporated with computing device 1150 (e.g., computing device 1150 can be configured as part of a device for capturing, scanning, and/or storing images). As another example, image source 1102 can be connected to computing device 1150 by a cable, a direct wireless link, and so on. Additionally or alternatively, in some embodiments, image source 1102 can be located locally and/or remotely from computing device 1150, and can communicate data to computing device 1150 (and/or server 1152) via a communication network (e.g., communication network 1154).

In some embodiments, communication network 1154 can be any suitable communication network or combination of communication networks. For example, communication network 1154 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, and so on. In some embodiments, communication network 1154 can be a local area network, a wide area network, a public network (e.g., the Internet), a private or semi-private network (e.g., a corporate or university intranet), any other suitable type of network, or any suitable combination of networks. Communications links shown in FIG. 11 can each be any suitable communications link or combination of communications links, such as wired links, fiber optic links, Wi-Fi links, Bluetooth links, cellular links, and so on.

Figure 12:
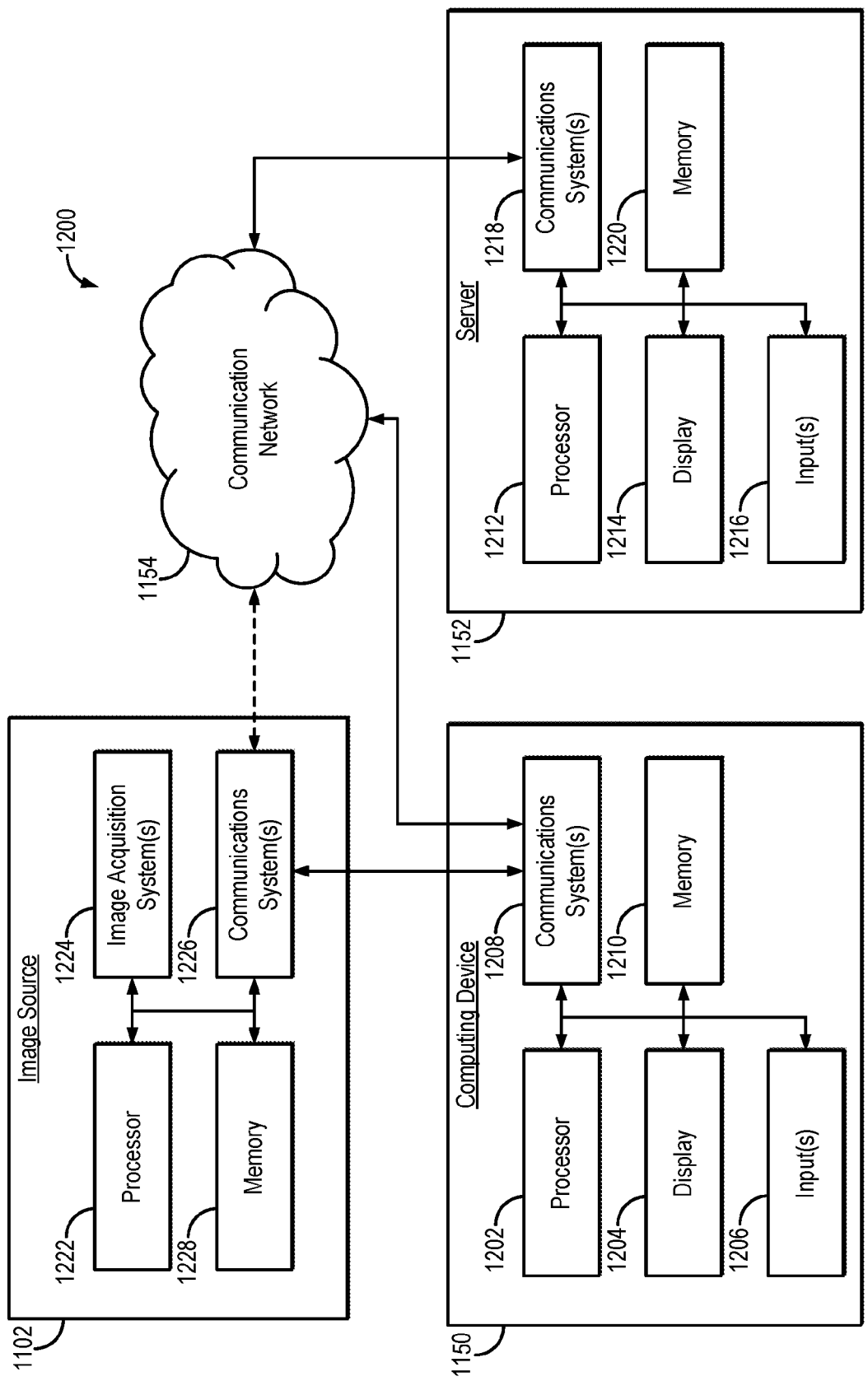
FIG. 12 is a block diagram of components that can implement the microvessel image generation system of FIG. 11.

Referring now to FIG. 12, an example of hardware 1200 that can be used to implement image source 1102, computing device 1150, and server 1152 in accordance with some embodiments of the systems and methods described in the present disclosure is shown. As shown in FIG. 12, in some embodiments, computing device 1150 can include a processor 1202, a display 1204, one or more inputs 1206, one or more communication systems 1208, and/or memory 1210. In some embodiments, processor 1202 can be any suitable hardware processor or combination of processors, such as a central processing unit ("CPU"), a graphics processing unit ("GPU"), and so on. In some embodiments, display 1204 can include any suitable display devices, such as a computer monitor, a touchscreen, a television, and so on. In some embodiments, inputs 1206 can include any suitable input devices and/or sensors that can be used to receive user input, such as a keyboard, a mouse, a touchscreen, a microphone, and so on.

In some embodiments, communications systems 1208 can include any suitable hardware, firmware, and/or software for communicating information over communication network 1154 and/or any other suitable communication networks. For example, communications systems 1208 can include one or more transceivers, one or more communication chips and/or chip sets, and so on. In a more particular example, communications systems 1208 can include hardware, firmware and/or software that can be used to establish a Wi-Fi connection, a Bluetooth connection, a cellular connection, an Ethernet connection, and so on.

In some embodiments, memory 1210 can include any suitable storage device or devices that can be used to store instructions, values, data, or the like, that can be used, for example, by processor 1202 to present content using display 1204, to communicate with server 1152 via communications system(s) 1208, and so on. Memory 1210 can include any suitable volatile memory, non-volatile memory, storage, or any suitable combination thereof. For example, memory 1210 can include RAM, ROM, EEPROM, one or more flash drives, one or more hard disks, one or more solid state drives, one or more optical drives, and so on. In some embodiments, memory 1210 can have encoded thereon, or otherwise stored therein, a computer program for controlling operation of computing device 1150. In such embodiments, processor 1202 can execute at least a portion of the computer program to present content (e.g., images, user interfaces, graphics, tables), receive content from server 1152, transmit information to server 1152, and so on.

In some embodiments, server 1152 can include a processor 1212, a display 1214, one or more inputs 1216, one or more communications systems 1218, and/or memory 1220. In some embodiments, processor 1212 can be any suitable hardware processor or combination of processors, such as a CPU, a GPU, and so on. In some embodiments, display 1214 can include any suitable display devices, such as a computer monitor, a touchscreen, a television, and so on. In some embodiments, inputs 1216 can include any suitable input devices and/or sensors that can be used to receive user input, such as a keyboard, a mouse, a touchscreen, a microphone, and so on.

In some embodiments, communications systems 1218 can include any suitable hardware, firmware, and/or software for communicating information over communication network 1154 and/or any other suitable communication networks. For example, communications systems 1218 can include one or more transceivers, one or more communication chips and/or chip sets, and so on. In a more particular example, communications systems 1218 can include hardware, firmware and/or software that can be used to establish a Wi-Fi connection, a Bluetooth connection, a cellular connection, an Ethernet connection, and so on.

In some embodiments, memory 1220 can include any suitable storage device or devices that can be used to store instructions, values, data, or the like, that can be used, for example, by processor 1212 to present content using display 1214, to communicate with one or more computing devices 1150, and so on. Memory 1220 can include any suitable volatile memory, non-volatile memory, storage, or any suitable combination thereof. For example, memory 1220 can include RAM, ROM, EEPROM, one or more flash drives, one or more hard disks, one or more solid state drives, one or more optical drives, and so on. In some embodiments, memory 1220 can have encoded thereon a server program for controlling operation of server 1152. In such embodiments, processor 1212 can execute at least a portion of the server program to transmit information and/or content (e.g., data, images, a user interface) to one or more computing devices 1150, receive information and/or content from one or more computing devices 1150, receive instructions from one or more devices (e.g., a personal computer, a laptop computer, a tablet computer, a smartphone), and so on.

In some embodiments, image source 1102 can include a processor 1222, one or more image acquisition systems 1224, one or more communications systems 1226, and/or memory 1228. In some embodiments, processor 1222 can be any suitable hardware processor or combination of processors, such as a CPU, a GPU, and so on. In some embodiments, the one or more image acquisition systems 1224 are generally configured to acquire data, images, or both, and can include an ultrasound imaging system. Additionally or alternatively, in some embodiments, one or more image acquisition systems 1224 can include any suitable hardware, firmware, and/or software for coupling to and/or controlling operations of an ultrasound imaging system. In some embodiments, one or more portions of the one or more image acquisition systems 1224 can be removable and/or replaceable.

Note that, although not shown, image source 1102 can include any suitable inputs and/or outputs. For example, image source 1102 can include input devices and/or sensors that can be used to receive user input, such as a keyboard, a mouse, a touchscreen, a microphone, a trackpad, a trackball, and so on. As another example, image source 1102 can include any suitable display devices, such as a computer monitor, a touchscreen, a television, etc., one or more speakers, and so on.

In some embodiments, communications systems 1226 can include any suitable hardware, firmware, and/or software for communicating information to computing device 1150 (and, in some embodiments, over communication network 1154 and/or any other suitable communication networks). For example, communications systems 1226 can include one or more transceivers, one or more communication chips and/or chip sets, and so on. In a more particular example, communications systems 1226 can include hardware, firmware and/or software that can be used to establish a wired connection using any suitable port and/or communication standard (e.g., VGA, DVI video, USB, RS-232, etc.), Wi-Fi connection, a Bluetooth connection, a cellular connection, an Ethernet connection, and so on.

In some embodiments, memory 1228 can include any suitable storage device or devices that can be used to store instructions, values, data, or the like, that can be used, for example, by processor 1222 to control the one or more image acquisition systems 1224, and/or receive data from the one or more image acquisition systems 1224; to images from data; present content (e.g., images, a user interface) using a display; communicate with one or more computing devices 1150; and so on. Memory 1228 can include any suitable volatile memory, non-volatile memory, storage, or any suitable combination thereof. For example, memory 1228 can include RAM, ROM, EEPROM, one or more flash drives, one or more hard disks, one or more solid state drives, one or more optical drives, and so on. In some embodiments, memory 1228 can have encoded thereon, or otherwise stored therein, a program for controlling operation of image source 1102. In such embodiments, processor 1222 can execute at least a portion of the program to generate images, transmit information and/or content (e.g., data, images) to one or more computing devices 1150, receive information and/or content from one or more computing devices 1150, receive instructions from one or more devices (e.g., a personal computer, a laptop computer, a tablet computer, a smartphone, etc.), and so on.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

The present disclosure has described one or more preferred embodiments, and it should be appreciated that many equivalents, alternatives, variations, and modifications, aside from those expressly stated, are possible and within the scope of the invention.

The invention claimed is:

1. A method for generating an image that depicts microvessels in a subject using an ultrasound system, the steps of the method comprising:
   (a) providing to a computer system, image data acquired from a subject with an ultrasound system, wherein the image data comprise image frames obtained at a plurality of different time points;
   (b) generating reformatted data with the computer system by reformatting the image data as a Casorati matrix;
   (c) generating motion matrix data with the computer system by computing a similarity metric of each column of the reformatted data with every other column of the reformatted data;
   (d) performing motion correction on the acquired image data by analyzing the motion matrix data with the computer system and based on this analysis generating updated image data by:
      (i) directing the ultrasound system to reject image data when analysis of the motion matrix data indicates translation motion occurred when the image data were acquired;
      (ii) directing the computer system to process the image data to reduce motion corruption when analysis of the motion matrix data indicates periodic motion occurred when the image data were acquired; and
   (e) generating an image that depicts microvessels in the subject by reconstructing the image from the updated image data using the computer system, wherein the image depicts fewer effects of motion based on the motion correction of the updated image data.

2. The method as recited in claim 1, further comprising generating from the motion matrix data, a data quality metric indicative of a quantitative measure of image data quality and providing the data quality metric to a user.

3. The method as recited in claim 2, wherein the data quality metric comprises a mean of the motion matrix data.

4. The method as recited in claim 2, wherein the data quality metric comprises a median of the motion matrix data.

5. The method as recited in claim 2, wherein providing the data quality metric to the user comprises generating a display that indicates the data quality metric.

6. The method as recited in claim 1, wherein steps (b)-(d) are performed in real-time as the image data are being acquired with the ultrasound system.

7. The method as recited in claim 1, wherein steps (b)-(d) are performed after the image data have been acquired with the ultrasound system.

8. The method as recited in claim 1, further comprising generating from the motion matrix data, a motion correction quality metric indicative of a quantitative measure of motion correction quality and providing the motion correction quality metric to a user.

9. The method as recited in claim 8, wherein the motion correction quality metric is based on a rank of the motion matrix data.

10. The method as recited in claim 1, wherein the reformatted data comprise a Casorati matrix, wherein each column of the Casorati matrix corresponds to a vectorized image frame obtained from a different time point.

11. The method as recited in claim 1, wherein the ultrasound system is directed to reacquire image data that are rejected when analysis of the motion matrix data indicates translation motion occurred when the image data were acquired.

12. The method as recited in claim 1, wherein the similarity metric is a correlation coefficient.

13. The method as recited in claim 1, wherein the similarity metric is a covariance metric.

14. The method as recited in claim 1, wherein the similarity metric is at least one of an angle or a magnitude of a column of the Casorati matrix.

15. The method as recited in claim 1, wherein the similarity metric is a distance metric.

16. The method as recited in claim 15, wherein the distance metric is one of a Euclidian distance, a Manhattan distance, a Mahalanobis distance, or a Minkowski distance.

17. The method as recited in claim 1, wherein analyzing the motion matrix comprises deciding frame-pairs in the image data and an optimal search window size for motion tracking within the image data.

18. The method as recited in claim 1, wherein processing the image data to reduce motion corruption includes analyzing the motion matrix to identify a reference frame for motion correction and reducing motion corruption in the image data based in part on the identified reference frame.

19. The method as recited in claim 18, wherein the reference frame is identified from the motion matrix as the image frame having a highest similarity metric with respect to other image frames in the image data.

20. The method as recited in claim 1, wherein analyzing the motion matrix comprises identifying image frames that experienced out-of-plane motion while the image data were acquired, and wherein the updated image data are generated by rejecting those image frames identified as experiencing out-of-plane motion.

21. The method as recited in claim 20, wherein identifying the image frames that experienced out-of-plane motion comprises identifying image frames from the motion matrix that are associated with low coherence.

22. The method as recited in claim 21, further comprising generating a spatiotemporal coherence map from the motion matrix and identifying the image frames that experienced out-of-plane motion using the spatiotemporal coherence map.

23. The method as recited in claim 22, wherein the updated image data are generated by rejecting only local spatial regions identified in the spatiotemporal coherence map as being associated with out-of-plane motion.

24. The method as recited in claim 1, further comprising estimating background noise field data from the motion matrix data using the computer system, and suppressing noise in the image by normalizing the image using the background noise field data.

25. The method as recited in claim 24, wherein the background noise field data are estimated by computing a synthetic noise image from the motion matrix data and estimating the background noise field data as a low-rank approximation of the synthetic noise image.

26. The method as recited in claim 25, wherein the synthetic noise image is computed by:
   generating a spatiotemporal correlation image from the motion matrix data, wherein pixel values in the spatiotemporal correlation image correspond to statistical measures of the motion matrix data;
   thresholding the spatiotemporal correlation image to separate flow pixels associated with flow from noise pixels associated with noise; and
   generating the synthetic noise image by replacing flow pixels in the spatiotemporal correlation image with noise pixels from the spatiotemporal correlation image.

27. The method as recited in claim 26, wherein each pixel value in the spatiotemporal correlation image is computed by computing a mean of motion matrix data in a local kernel centered on that pixel.

28. The method as recited in claim 26, wherein generating the synthetic noise image comprises replacing each flow pixel with a noise pixel randomly selected from a local neighborhood of the flow pixel.

29. The method as recited in claim 28, wherein the local neighborhood comprises at least one of pixels across rows, columns, or frames.

30. The method as recited in claim 25, wherein the low-rank approximation is based on a singular value decomposition.

\* \* \* \* \*